US012635904B2

(12) United States Patent (10) Patent No.: US 12,635,904 B2

Nelson et al. (45) Date of Patent: May 26, 2026

(54) SYSTEMS AND METHODS FOR MONITORING SUBJECTS

(71) Applicant: Hillrom Services, Inc., Batesville, IN (US)

(72) Inventors: Christopher Nelson, Batesville, IN (US); Dan R. Tallent, Batesville, IN (US)

(73) Assignee: Hillrom Services, Inc., Batesville, IN (US)

(*) Notice: Subject to any disclaimer, the term of this patent is extended or adjusted under 35 U.S.C. 154(b) by 12 days.

(21) Appl. No.: 18/581,958

(22) Filed: Feb. 20, 2024

(65) Prior Publication Data

US 2024/0277255 A1 Aug. 22, 2024

Related U.S. Application Data

(60) Provisional application No. 63/486,105, filed on Feb. 21, 2023.

(51) Int. Cl.
*A61B 5/091* (2006.01)
*A61B 5/00* (2006.01)
(Continued)

(52) U.S. Cl.
CPC ............ *A61B 5/091* (2013.01); *A61B 5/0077* (2013.01); *A61B 50/13* (2016.02); *A61B 50/20* (2016.02); *G06T 7/0012* (2013.01); *G06T 7/62* (2017.01); *G06T 7/70* (2017.01); *G16H 20/10* (2018.01); *G16H 30/40* (2018.01);
(Continued)

(58) Field of Classification Search
CPC ......... A61B 5/091; A61B 50/13; A61B 5/163; G16H 40/67
See application file for complete search history.

(56) References Cited

U.S. PATENT DOCUMENTS 9,295,390 B2 3/2016 Receveur
10,259,119 B2 4/2019 Wang
(Continued)

FOREIGN PATENT DOCUMENTS

CN 205729326 U 11/2016
CN 111481368 A 8/2020
(Continued)

OTHER PUBLICATIONS

"Real-time motorized electrical hospital bed control with eye-gaze tracking" by N.A. Atasoy et al. Turkish J Electric Eng Comp Sci. vol. 24, No. 6. pp. 5162-5172 (2016).*

*Primary Examiner* — Jason M Ip
(74) *Attorney, Agent, or Firm* — Dinsmore & Shohl LLP

(57) ABSTRACT

Disclosed herein are vision systems. The vision systems may be integrated into person support apparatuses, or may be integrated into mobile carts such that the vision systems are movable relative to the person support apparatus. The vision system includes at least one camera positioned such that a field of view of the at least one camera contains the person support apparatus and the subject positioned thereon. The vision system also includes a computer communicatively coupled to the at least one camera. The computer is configured to receive at least one image from the at least one camera and determine a tidal volume of the subject positioned on the person support surface from the at least one image.

10 Claims, 8 Drawing Sheets

(51) Int. Cl.

| | |
|---|---|
| *A61B 50/13* | (2016.01) |
| *A61B 50/20* | (2016.01) |
| *G06T 7/00* | (2017.01) |
| *G06T 7/62* | (2017.01) |
| *G06T 7/70* | (2017.01) |
| *G16H 20/10* | (2018.01) |
| *G16H 30/40* | (2018.01) |
| *H04N 23/695* | (2023.01) |
| *H04N 23/54* | (2023.01) |

(52) U.S. Cl.
CPC . *H04N 23/695* (2023.01); *G06T 2207/30004* (2013.01); *G06T 2207/30196* (2013.01); *H04N 23/54* (2023.01)

(56) References Cited

U.S. PATENT DOCUMENTS

| | | | |
|---|---|---|---|
| 10,381,116 | B2 | 8/2019 | Zerhusen |
| 10,874,567 | B2 | 12/2020 | Zerhusen |
| 10,904,492 | B2 | 1/2021 | Derenne |
| 11,633,103 | B1* | 4/2023 | Nudd ...................... G06F 17/18 |
| | | | 704/9 |
| 2009/0105551 | A1* | 4/2009 | Kelch ................... F16M 11/04 |
| | | | 600/300 |
| 2011/0218674 | A1* | 9/2011 | Stuart ................... H04L 65/403 |
| | | | 700/259 |
| 2013/0314522 | A1* | 11/2013 | Ravid ...................... H04N 7/18 |
| | | | 348/77 |
| 2017/0014051 | A1 | 1/2017 | Matsumoto |
| 2022/0108114 | A1 | 4/2022 | Yoshida |
| 2022/0133156 | A1* | 5/2022 | Hartley ............... A61B 5/7264 |
| | | | 600/301 |
| 2022/0244779 | A1* | 8/2022 | Takamoto ................. G06T 7/97 |
| 2023/0293017 | A1 | 9/2023 | Hille |

FOREIGN PATENT DOCUMENTS

| | | |
|---|---|---|
| CN | 212368969 U | 1/2021 |
| CN | 213373148 U | 6/2021 |
| CN | 114081453 A | 2/2022 |
| WO | 2021245132 A1 | 12/2021 |

* cited by examiner

520

Record the subject and one or more objects in the room simultaneously with the same camera — 522

Determine a gaze direction of the subject — 524

526 — Determine whether the gaze direction of the subject is directed towards the one or more objects

NO

YES

Output a notification if the gaze direction is associated with the one or more objects — 528

SYSTEMS AND METHODS FOR MONITORING SUBJECTS

CROSS-REFERENCE TO RELATED APPLICATION

The present application claims the priority benefit of U.S. Provisional Application Ser. No. 63/486,105, entitled "Systems and Methods for Monitoring Subjects" and filed Feb. 21, 2023, the entire contents of which are incorporated herein.

TECHNICAL FIELD

The present disclosure relates to systems and methods for monitoring subjects and, more specifically, to systems and methods for capturing images of a subject and determining information from the captured images.

BACKGROUND

Medical facilities such as hospitals may utilize camera systems for remotely observing subjects. These systems may be utilized, for example, for monitoring if a subject is about to get out of bed and/or for monitoring the subject's vital signs. A drawback of existing camera systems is that they are bulky and thereby require clinicians to work around yet another piece of equipment in an already crowded space. For example, existing camera systems may be mounted on a mobile stand which sits near the bed. In some cases, depending on the intended application of the camera system, the camera thereof needs to be within a close proximity of the subject which further exacerbates the challenges of equipment getting in the way of normal clinical workflow. To remedy this deficiency, some camera systems include wall or ceiling mounted cameras such that they are out of the way of clinicians. However, with these systems, the large distance between the wall or ceiling mounted camera and the subject may be too great for effective monitoring of particular subject parameters. Further, medical facilities may struggle with accurately tracking subjects, for example, tracking how long a subject has been in a particular care department (e.g., radiology) during their stay at the medical facility and/or tracking when and for how long a subject has left the bed. Moreover, some subjects may not have an ability to verbally communicate, and, in these situations, subjects may have needs that are not readily recognized by the clinical staff.

SUMMARY

In one embodiment, a vision system includes at least one camera and a computer. The at least one camera is positioned such that a field of view of the at least one camera contains a person support apparatus supporting a subject positioned thereon. The computer is communicatively coupled to the at least one camera, and the computer is configured to receive at least one image from the at least one camera and determine a tidal volume of the subject positioned on the person support surface from the at least one image.

In another embodiment, a vision system includes a first camera, a second camera, and a computer. The first camera is positioned such that a field of view of the first camera contains a person support apparatus supporting a subject positioned therein. The second camera is positioned such a field of view of the second camera contains an object therein. The computer is communicatively coupled to the first camera and the second camera. The computer is configured to receive at least one image from the first camera and determine a gaze direction of a subject from the at least one image from the first camera, receive at least one image from the second camera and determine a location of the object, determine whether the subject is looking at the object based on the gaze direction of the subject and the location of the object, and output a notification when the of the subject is looking at the object.

In another embodiment, a vision system for a person support apparatus includes at least one camera, and a computer. The at least one camera is positioned such that a field of view of the at least one camera contains both an object and the person support apparatus supporting a subject positioned therein. The computer is communicatively coupled to the at least one camera. Further, the computer is configured to receive at least one image from the at least one camera and determine a gaze direction of the subject and a location of the object from the at least one image from the first camera, determine whether the subject is looking at the object based on the gaze direction of the subject and the location of the object, and output a notification when of the subject is looking at the object.

In yet another embodiment, a method of determining tidal volume of a subject on a person support apparatus is disclosed. The method may include receiving, at a computer, image data from a camera communicatively coupled to the computer, wherein the camera is positioned such that a field of view of the camera contains a display of a health monitor associated with the subject and the image data is indicative the tidal volume of the subject presented on the display of the health monitor. The method may also include determining, via the computer, the tidal volume of the subject positioned on the person support surface based on the image data received from the camera, and outputting the tidal volume of the subject.

In another embodiment, a vision system includes at least one camera and a computer communicatively coupled to the at least one camera. The at least one camera is positioned such that a field of view of the at least one camera contains a person support apparatus supporting a subject positioned thereon. The computer is configured to receive at least one image from the at least one camera, determine whether the subject is present on the person support surface from the at least one image, and generate an alert indicating that the subject is not present on the person support surface. The computer stores an algorithm for determining a gaze of the subject, determining that a target of the gaze of the subject corresponds to a location of an object, and outputting a notification indicating that the subject is viewing the object.

In yet another embodiment, a vision system includes a computer configured to receive image data and determine a tidal volume of the subject positioned on a person support surface from the image data. The computer is further configured to determine, using the image data, status of health parameters and/or occurrence of a medical event.

In yet another embodiment, a method of determining tidal volume of a subject on a person support apparatus is disclosed. The method may include receiving, at a computer, image data indicative the tidal volume of the subject. Also, the method may include determining, via the computer, the tidal volume of the subject positioned on the person support surface based on the image data received at the computer, and outputting the tidal volume of the subject.

In yet another embodiment, a vision system includes at least one camera and a computer communicatively coupled to the at least one camera. The at least one camera is positioned such that a field of view of the at least one camera contains a person support apparatus supporting a subject positioned thereon. The computer is configured to receive at least one image from the at least one camera, determine whether the subject is within a predetermined distance from an edge of the person support surface, and generate an alert indicating that the subject is at risk of falling off of the person support surface upon determining that the subject is within the predetermined distance from the edge.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
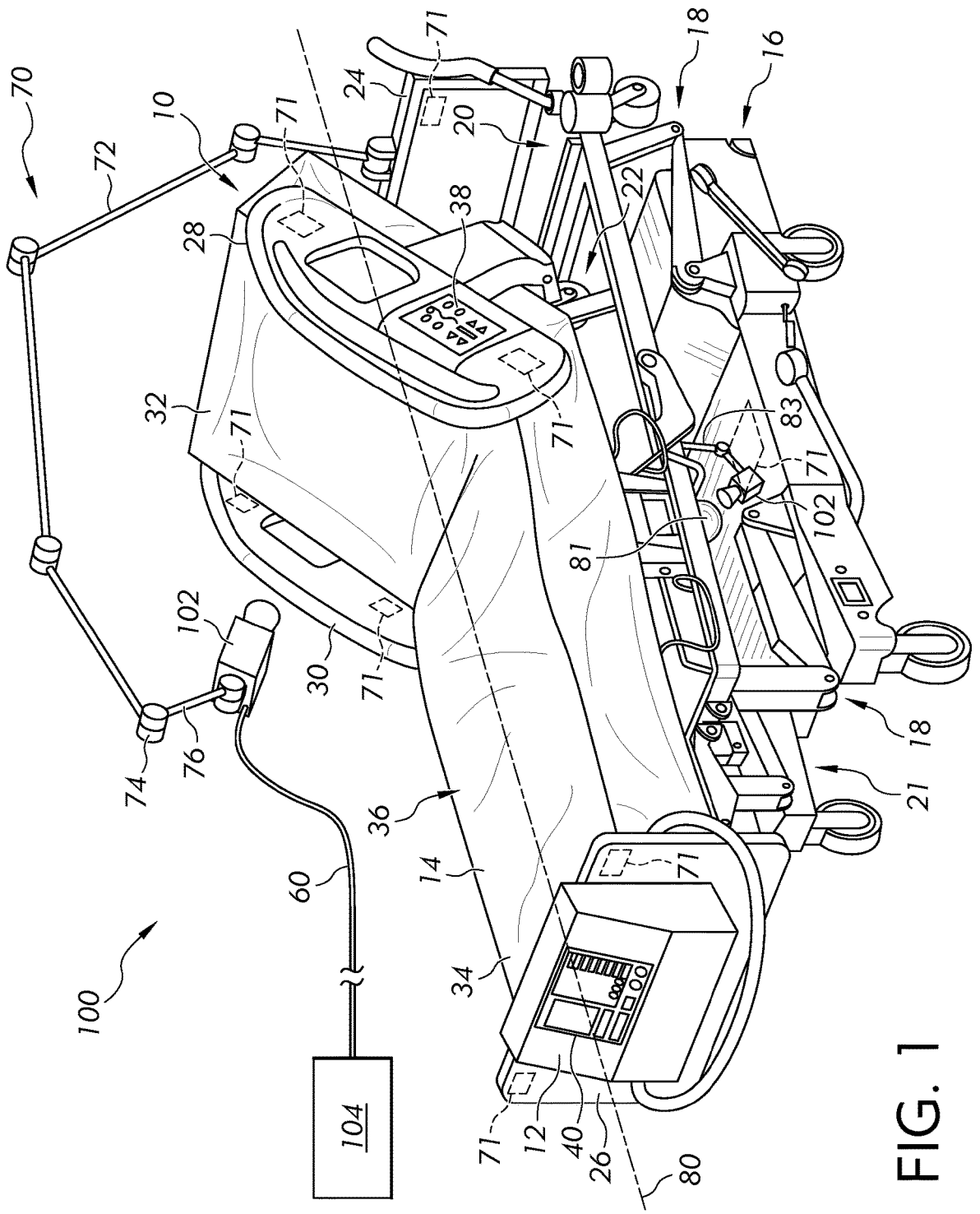
FIG. 1 depicts a perspective view of an illustrative person support apparatus including a vision system, according to one or more embodiments shown and described herein.

Embodiments described herein are directed to vision systems for person support apparatuses and methods for utilizing vision systems to optimize care of a subject on or assigned to the person support apparatus. The vision systems described herein include a computer and a camera communicatively coupled to the computer. The camera may be mounted at various locations on the person support apparatus, such as the foot or head board thereof. The camera is modular, such that it may be moved to different mounting locations. In embodiments, the camera is obscurable or camouflageable such that the camera is not readily apparent to the subject so as to reduce anxiety in subjects. The camera may be automatically or manually movable to adjust a field of view of the camera, or the computer may be operable to move the camera or adjust the field of view of the camera. The camera may be positioned such that its field of view contains the bed and areas surrounding the bed, such that the computer is able to monitor the subject and positioning of the subject, monitor vital signs (e.g., SpO2, tidal volume), and monitor medication levels. The camera may be swappable with other cameras and/or devices having varying features. In embodiments, the computer determines vital signs (e.g., SpO2, tidal volume) and/or medication levels based on data from the camera. The computer may be a standalone component or mounted to the person support apparatus. The computer includes data storage hardware and networking hardware. Data pulled from the camera is usable to provide a live stream, and may be combined with data from other cameras and/or non-camera sensors. Data from the camera may be utilized with facial recognition algorithms or the like to determine identity of the subject and/or associate the subject with a particular person support apparatus or particular room. In embodiments, the vision system may determine where the subject is looking, so as to provide a means of non-verbal communication with the subject.

Various embodiments of the person support apparatus and methods for operation of the person support apparatus are described in more detail herein. Whenever possible, the same reference numerals will be used throughout the drawings to refer to the same or like parts.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom, upper, lower—are made only with reference to the figures as drawn and are not intended to imply absolute orientation. The terms "proximal" and "distal" are defined herein relative to a subject on a person support apparatus. The term "distal" refers to the position of an element that is closer to the subject and the term "proximal" refers to the position of an element that is further away from the subject.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

FIG. 1 illustrates a vision system 100 utilizable with a person support apparatus 10, according to one or more embodiments of the present disclosure. The person support apparatus 10 includes a person support surface 14. In the illustrated embodiment, the person support apparatus 10 is a bed and the person support surface 14 is a mattress. The person support apparatus 10 includes a base frame 16, an intermediate frame 20 coupled to the base frame 16 by linkages 18, and an articulating deck frame 22 that is coupled to the intermediate frame 20 and that supports the person support surface 14. The person support apparatus 10 also includes a head end 24, a foot end 26, a left side rail 28, and a right side rail 30. In the illustrated example, the left side rail 28 is positioned at a left edge of the person support apparatus 10, such that the left side rail 28 and the right side rail 30 is positioned at a right edge of the person support apparatus, such that the left side rail 28 and the right side rail 30 are operable to help maintain the subject on the person support surface 10 and help prevent the subject from falling off the person support surface 10, for example, by or rolling or turning over the left edge or right edge, respectively. A longitudinal axis 80 extends from the head end 24 to the foot end 26. The articulating deck frame 22 includes separate sections that articulate relative to the base frame 16 and relative to each other, for example, a mattress center section 36 that is height adjustable, and a mattress head section 32 and a mattress foot section 34 that are adjustable in elevation relative to the mattress center section 36. A control panel 38 is used to actuate and control articulation of the articulating deck frame 22. While the illustrated embodiment illustrates the left side rail 28 and the right side rail 30 extending along the mattress head section 32, either or both of the left side rail 28 and the right side rail 30 may also extend along either or both of the mattress center section 36 and the mattress foot section 34 in addition to or in lieu of extending along the mattress head section 32. In embodiments, rails (not illustrated) are provided at the head end 24 and/or the foot end 26 as illustrated with respect to the left side rail 28 and the right side rail 30.

In the illustrated embodiment, a control system 12 is provided on the person support apparatus 10. The control system 12 includes a user interface 40 for controlling various components and/or features of the person support surface 14, such as different onboard sensor systems and or therapy systems that may be incorporated into the person support apparatus 10.

In the illustrated embodiment, a vision system 100 is integrated with the person support apparatus 10 for monitoring and optimizing care of a subject on the person support surface 14. The vision system 100 includes at least one camera 102 and a computer 104 communicatively coupled to the at least one camera 102. In the illustrate example, the computer 104 is provided as a separate component from the person support apparatus 10. Accordingly, the computer 104 may be located in a different room than the person support apparatus 10, for example, in room dedicated for computer and server equipment. Alternatively, the computer 104 may be provided on a mobile cart that may be moved into proximity of the person support apparatus 10 on an as needed or as desired basis. In other embodiments, the computer 104 may be fixed to the person support apparatus 10, for example, the computer 104 may be integrated within the control system 12 of the person support apparatus 10. Also, in the illustrated embodiment, the at least one camera 102 communicates with the computer 104 via a cable 60. In other embodiments, the at least one camera 102 and the computer 104 may communicate wirelessly. While FIG. 1 illustrates the at least one camera 102 as a single camera, the at least one camera 102 may include a plurality of cameras, as described below, and each of the cameras are communicatively coupled to the computer 104 via wired and/or wireless communication.

The at least one camera 102 may be supported by the person support apparatus 10 and/or by some external means. In the illustrated embodiment, the at least one camera 102 is supported by a boom 70 that is coupled to person support apparatus 10. Here, the boom 70 is supported on the head end 24 of the person support apparatus 10, with a first end of the boom 70 being coupled to the head end 24 and a second end of the boom 70 being coupled to the at least one camera 102. In other embodiments, the at least one camera 102 may be provided on a mobile cart that may be moved into proximity of the person support apparatus 10 on an as needed or as desired basis and, in some embodiments, the at least one camera 102 and the computer 104 are provided on the same mobile cart. The at least one camera 102 may be coupled to the mobile cart via the boom 70 in a similar manner as described with reference to the person support apparatus 10.

In other embodiments, the boom 70 may be coupled to the foot end 26, the left side rail 28, and/or the right side rail 30. In embodiments where the at least one camera 102 includes two or more cameras, each camera may be supported by the same boom or separate booms, and such same or separate booms may be coupled to the foot end 26, the left side rail 28, the right side rail 30, and/or from another structure (e.g., ceiling, wall, furniture, etc.). Thus, the person support apparatus 10 may include a plurality of mounting sites 71 for mounting the boom 70 and/or the at least one camera 102, and the at least one camera 102 and/or the boom 70 may be mounted at any one or more of the mounting sites 71 about the person support apparatus 10. While FIG. 1 depicts the mounting sites 71 at particular locations on the person support apparatus 10, it should be understood that these locations are merely illustrative and the present disclosure is not limited to such locations. Regardless of where the at least one camera 102 and the boom 70 are mounted, the at least one camera 102 is oriented such that the subject is within a field of view of the at least one camera 102, including when the subject may reposition themselves on the person support surface 14, incline or decline the person support surface 14, etc. In embodiments, the boom 70 and the at least one camera 102 are coupled to the mattress head section 32 such that the boom 70 and the at least one camera 102 move with the mattress head section 32 as it is inclined or declined. In other embodiments, the computer 104 may be in communication with the control panel 38 (or a controller of the control panel 38) utilized to control articulation of the articulating deck frame 22 (e.g., by sending a control signal to the articulating deck frame 22 instructing the articulating deck frame 22 to incline or decline), such that the computer 104 automatically moves the boom 70 to adjust the position and/or orientation of the at least one camera 102 based on movement of the articulating deck frame 22 to ensure that the subject remains in the field of view of the camera at least one 102 as the mattress head section 32 inclines and/or declines. In embodiments the at least one camera 102 is focused on something other than the subject, as described below, the computer 104 may automatically orient the at least one camera 102 in a similar manner to maintain its focus on that other item.

In the illustrated embodiment, the boom 70 includes a plurality of linkage arms 72 interconnected and coupled to each other via a plurality of rotational joints 74, and the at least one camera 102 is supported on a distal most linkage arm 76 of the plurality of linkage arms 72. In embodiments, the distal most linkage arm 76 is a gimbal (e.g., a three axis gimbal) from which the at least one camera 102 is suspended. The rotational joints 74 may each include an individual motor that is in communication with the computer 104, such that the computer 104 is operable to control movement of the rotational joints 74 that are motorized. In this manner, each of the rotational joints 74 is separately controllable so as to articulate the linkage arms 72 in a plurality of degrees of freedom and thereby to position the at least one camera 102 in a desired orientation relative to the subject. Accordingly, the boom 70 may operate as a robotic arm. However, less than all of the rotational joints 74 may be motorized. For example, in some embodiments, the rotational joints 74 are not motorized, such that the boom 70 operates as an extendible arm that may move relative to the person support apparatus 10. In embodiments, the boom 70 may be folded up and stowed so that it is not obstructing the space surrounding the person support apparatus 10, for example, it may be folded and stowed underneath the person support apparatus 10, and this feature may be incorporated regardless of whether or not the rotational joints 74 are motorized. In embodiments, the computer 104 is operable to control actuation of at least some of the rotational joints 74 to thereby adjust the field of view of the at least one camera 102 based on an orientation of a person support surface 14 (e.g., whether inclined or declined) of the person support apparatus 10 as sensed by the at least one camera 102. Thus, the computer 104 may utilize feedback or data that is received from the at least one camera 102 and indicative of an orientation of the articulating deck frame 22 to thereby move or adjust position of the field of view of the at least one camera 102. In embodiments, the computer 104 may utilize feedback or data from the articulating deck frame 22 or the control panel 38 associated therewith to move or adjust position of the field of view of the at least one camera 102. For example, in embodiments, the computer 104 may be in communication with motors of each of the rotational joints 74 as well as the control panel 38 utilized to control articulation of the articulating deck frame 22, such that the computer 104 causes actuation of the rotational joints 74 to adjust the position and/or orientation of the boom 70 and the at least one camera 102 based on movement of the articulating deck frame 22, to thereby ensure that the subject remains in the field of view of the at least one camera 102 as the mattress head section 32 inclines and/or declines. In embodiments, any one or more of the at least one camera 102 may also be oriented such that its/their field of view captures or is focused on things, such as views of the subject's medications (e.g. amount of medication remaining in an IV bag) and/or views of health monitors within the room (e.g. SpO2, respiration rate, ECG, NIBP, temperature, EtCO2, blood pressure, etc.). Also, by utilizing one or more additional cameras focused on the subject, a three dimensional (3-D) view of the subject may be developed, which 3-D view may provide additional information as to the subject's orientation/positioning on the person support surface 14, as well as the subject's tidal volume (i.e., with each breath), total mass/change in mass, etc.

The at least one camera 102 may be supported at various other locations about the person support apparatus 10, in addition to or instead of the at least one camera 102 being mounted to the person support surface via the boom 70, as described above. For example, the at least one camera 102 may be coupled to the base frame 16, the intermediate frame 20, and/or the articulating deck frame 22. In embodiments, the at least one camera 102 is coupled to person support apparatus 10 at a location between base frame 16 and the articulating deck frame 22. In embodiments, the at least one camera 102 is coupled to a lower surface 21 of the person support surface 14 that is opposite the mattress. In embodiments, the at least one camera 102 is mounted within the left side rail 28 and/or the right side rail 30.

In embodiments, a mirror 81 (e.g., a mirrored dome) is mounted to the lower surface 21 of the person support surface 14 or a lower surface of the articulating deck frame 22. The mirror 81 may be mounted thereto in any suitable manner such as by fasteners, adhesives, or the like. The mirror 81 includes a reflective outer surface which allows the mirror 81 to reflect light in a complete 360 degree field of view around the person support apparatus 10. As further described, utilization of the mirror 81 enables the at least one camera 102 to obtain an enlarged and redirected field of view around the person support apparatus 10. In these embodiment, the at least one camera 102 may be mounted such that the mirror 81 is within the field of view of the at least one camera 102, for example, the at least one camera 102 may be mounted on an upper surface of the base frame 16 such that the at least one camera 102 is directed towards and faces the mirror 81. In the illustrated embodiment, the at least one camera 102 is located directly below the mirror 81, between the mirror 81 and the base frame 16, and oriented such that the field of view of the at least one camera 102 is directed in an upward vertical direction towards the mirror 81. In these embodiments, the at least one camera 102 may be supported by a mounting arm 83. The mounting arm 83 may be provided similar to as described with regard to the boom 70 such that the mounting arm 83 allows for adjustment of the at least one camera 102, or the mounting arm 83 may be a fixed and rigidly support the at least one camera 102 in a fixed orientation. Additionally, it should be appreciated that the mounting arm 83 may be thin in cross section and/or constructed of transparent material to prevent substantial obstruction of light directed on to or reflected off the mirror 81. Here, the at least one camera 102 has a field of view that is wide enough to capture image data of the entire outer surface of the mirror 81, for example, the field of view of at least one camera 102 may extend across an entire diameter of the mirror 81 (e.g., configured as a mirrored dome) so that the entire outer surface thereof may be viewed by the at least one camera 102. Accordingly, the at least one camera 102 is able to capture images of any object in the area surrounding the person support apparatus 10 below a plane defined by the lower surface 21 based on light that is incident on the outer surface of the mirror 81. It should be appreciated that light from certain objects may be obstructed from being incident on and reflected by the outer surface of the mirror 81 by the mounting arm 83 or other components of the person support apparatus 10 extending between the articulating deck frame 22 and the base frame 16. Accordingly, the at least one camera 102 collects image data of an area surrounding the person support apparatus 10 below the plane corresponding with the lower surface 21. As described in more detail herein, the image data is transmitted to the computer 104 (FIG. 2), which processes the image data.

The at least one camera 102 is configured to capture images in any electromagnetic frequency range, including the infra-red spectrum and the visible spectrum. That is, the at least one camera 102 may include various types of cameras and/or optical sensors. For example, the at least one camera 102 may include various types of optical sensors, including RGB, IR, FLIR, LIDAR optical sensors, or a combination thereof. Where the at least one camera 102 includes a plurality of cameras. The cameras may be of the same type, or may be of two or more different types. In embodiments, the at least one camera 102 may be configured to capture still images and/or video. Because the at least one camera 102 is modular, it may be swapped with other types of cameras as may be desired based on the clinical needs of the subject. For example, an RGB camera may remove from the boom 70 (or one of the booms 70) and replaced with a IR camera. The at least one camera 102 may capture still images, a plurality of images over a predetermined time period, and/or video.

In embodiments, the at least one camera 102 is removable from the distal most linkage arm 76 and/or the rotational joint 74 provided thereon. In embodiments, the boom 70 is removable from the person support apparatus 10 and may, for example, be attached to other equipment and/or furniture proximate to the person support apparatus 10. While the boom 70 is illustrated attached to the foot end 26 of the person support apparatus 10, it may be attached to different portions or structures of the person support apparatus 10. Also, even though the boom 70 may be robotically controlled, it may be manually moved, for example, by a nurse or caretaker, so as to reposition the at least one camera 102 as may be desired. As mentioned, the at least one camera 102 of the vision system 100 may include a plurality of cameras and, where utilized, any one or more of the cameras may be supported by the boom 70. In embodiments, at least some of those additional cameras may be mounted such that their fields of view capture the environment around the person support apparatus 10, such as items in a hospital room (or corridor) and/or other subjects that may be located in the path that the person support apparatus 10 is moving (i.e., during transport), which may be useful for detecting object detections and/or identifying positioning of people/objects with relation to the subject.

Regardless of whether the at least one camera 102 is supported by a structure, such as the boom 70, or is directly mounted to a portion of the person support apparatus 10, the at least one camera 102 may be mounted in a modular fashion so that it can be easily replaced and/or swapped. Also, where the at least one camera 102 has been removed from the boom 70 and/or some other mounting structure, a cover may be provided or placed over an empty slot of the boom 70 or other mounting structure so that the empty slot appears more aesthetically pleasing. Additionally, if a cover is utilized, a more continuous surface is easier to clean/ sterilize than an empty slot.

Because some subjects may exhibit anxiety when being imaged by the at least one camera 102, especially when in close proximate to the at least one camera 102, the at least one camera 102 and/or its optics may be camouflaged. For example, the at least one camera 102 may be integrated within a portion of the person support apparatus 10, and some components of the at least one camera 102 may be hidden, embedded, or otherwise obscured with opaque covers (e.g., glass with dark colors) or the like such that the cameras are indistinguishable from the mounting surface. In embodiments, the at least one camera 103 is integrated and embedded in the left side rail 28, the right side rail 30, the head end 24, and/or the foot end 26 of the person support apparatus 10.

Figure 2:
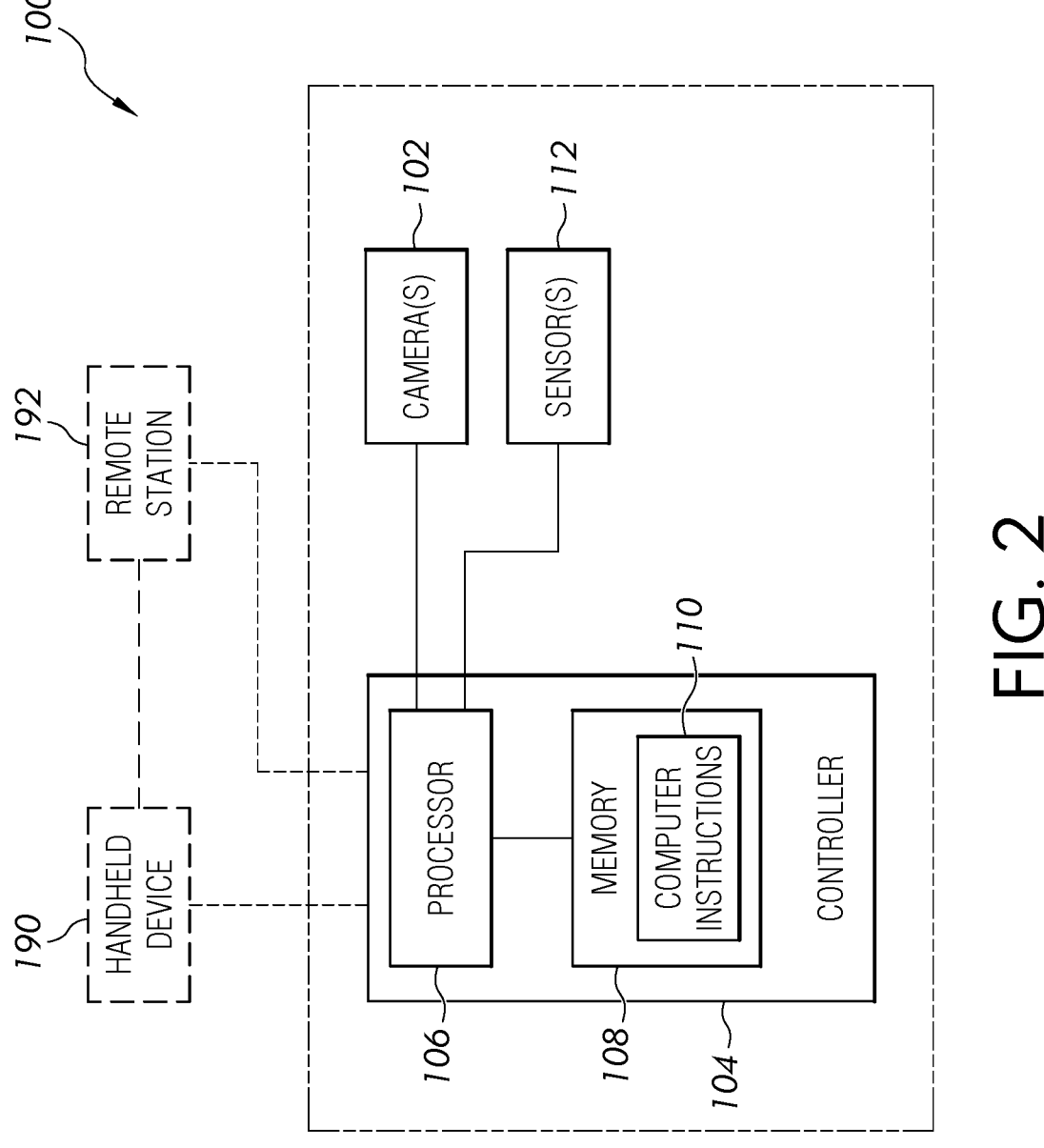
FIG. 2 schematically depicts the vision system, according to one or more embodiments shown and described herein.

FIG. 2 illustrates a block diagram of the vision system 100, according to one or more embodiments of the present disclosure. As mentioned above, the vision system 100 generally includes the computer 104. The computer 104 may be communicatively coupled to at least one monitor. In some embodiments, the at least one monitor may include, for example and without limitation, at least one handheld device 190 and/or at least one remote station 192. The computer

104 includes at least one processor 106 and at least one non-transitory memory module 108 (hereinafter, the memory 108) that are communicatively coupled to one another. The memory 108 includes computer readable and executable instructions 110 that may be executed by the processor 106. Accordingly, it should be understood that the at least one processor 106 may be any device capable of executing the computer readable and executable instructions 110. For example, the processor 106 may be a controller, an integrated circuit, a microcontroller, a computer, or any other computing device.

As mentioned, the vision system 100 includes the at least one camera 102. As shown, the at least one camera 102 is communicatively coupled to the processor 106 for monitoring the subject and optimizing care of the subject as herein described. The vision system 100 may further at least one sensor 112 communicatively coupled to the processor 106 for monitoring health parameters of the subject. The processor 106 of the computer 104 is also communicatively coupled to the at least one sensor 112.

The vision system 100 also includes a power source. In embodiments, the person support apparatus 10 includes a power source and the vision system 100 draws power (is powered by) the power source of the person support apparatus 10. In other embodiments, the vision system 100 includes a power source that is external or separate from the person support apparatus 10.

The at least one handheld device 190 and the at least one remote station 192 are remote devices that may each be communicatively coupled to the computer 104 and may each be communicatively coupled to each other. The at least one remote station 192 may include a processor and a non-transitory memory module that are communicatively coupled to one another, wherein the non-transitory memory module of the at least one remote station 192 includes computer readable and executable instructions that may be executed by the processor of the at least one remote station 192. The at least one remote station 192 may include one or more displays for outputting data for viewing by the subject and/or caregivers, as hereinafter described. Similarly, the at least one handheld device 190 may include a processor and a non-transitory memory module that are communicatively coupled to one another, wherein the non-transitory memory module of the at least one handheld device 190 includes computer readable and executable instructions that may be executed by the processor of the at least one handheld device 190. Also, the at least one handheld device 190 may include one or more displays for outputting data for viewing by the subject and/or caregivers, as hereinafter described. In embodiments, the at least one handheld device 190 includes a plurality of handheld devices and/or the at least one remote station 192 includes a plurality of remote stations. In embodiments, the initialization of the vision system 100 may be achieved via the at least one handheld device 190 and/or the at least one remote station 192. In embodiments, the at least one handheld device 190 and the at least one remote station 192 may stream data from the at least one camera 102 and/or the at least one sensor 112. In embodiments, the at least one handheld device 190 and/or the at least one remote station 192 are operable to control operation of the vision system 100 and/or operable to control operation or positioning of at least one camera 102.

In embodiments, the sensors are worn by the subject. In embodiments, the sensors are positioned on the person support apparatus 10. Fr example, the sensors may be positioned on the left side rail 28 and/or the right side rail 30, and/or may be positioned at the head end 24 (e.g., at a headboard) and/or at the foot end 26 (e.g., at a footboard) of the person support apparatus 10. The sensors may include temperature sensors, infrared sensors, pressure sensors, capacitive sensors, inductive sensors, optical sensors, load beams, load cells, moisture sensors, etc. The sensors may be configured to measure or sense physiological conditions or biomarkers of the subject, for example, such as oxygen saturation (SpO2), skin degradation, heart rate or pulse rate, blood pressure, etc. As mentioned, the sensors may include wearable sensors, such as transdermal wearable sensors, optical wearable sensors, and mechanical wearable sensors. Examples of such mechanical wearable sensors include piezoelectric sensors, piezoresistive sensors, piezocapacitive sensors, and triboelectric sensors. With regard to skin degradation, a sensor may be provided that measures moisture on the subject's skin. Also with regard to skin degradation, a sensor may be provided that measures or monitors skin color, swelling, temperature, and/or damage. For example, a sensor for measuring/sensing skin degradation may include a thermal camera that captures changes in skin temperature over a particular time period (e.g. over the course of the subject's stay in a medical facility). Such a thermal camera could be installed such that it continuously captures data about the subject, or such thermal camera could be utilized by the caregiver to actively take an image of an area of skin or suspected injury on as needed or as desired basis, or such thermal camera may be configured to capture video at certain times, such as passive video or image capture during sheet changes. Any one or more of the at least one sensor may be integrated within the person support apparatus 10. For example, where the at least one sensor 112 includes load sensors (or load cells or load beams), such items may be integrated within the person support surface 14.

In one example, the at least one sensor 112 includes an infrared detector and a temperature sensor, with the processor 106 of the computer 104 being communicatively coupled to both the infrared detector and temperature sensor. Here, the computer 104 may be configured and operable to determine, using data received from the infrared detector and the temperature sensor (and/or any other sensor), whether the subject is experiencing a medical condition or whether the subject's health parameters are in a normal or healthy range. For example, the computer 104 may be configured to determine whether the subject has experienced a change in core temperature that exceeds a predetermined temperature threshold relative to a baseline core temperature of the subject. Then, the computer 104 may generate and transmit an alert to or through one or more of the at least one handheld device 190 and the at least one remote station 192 when the determined core temperature of the subject exceeds the predetermined temperature threshold. In other embodiments, the computer 104 may transmit the core temperature of the subject to the at least one remote station 192, and the at least one remote station 192 thereby determines whether the core temperature of the subject exceeds the predetermined temperature threshold and, in that instance, the at least one remote station 192 outputs an alert through the at least one handheld device 190, the at least one remote station 192, and/or both. The alert may be in the form of an audible message, a visual display, and/or a tactile feedback, etc.

In embodiments where the at least one camera 102 is focused on a health monitor of the subject and/or on subject's medications (e.g. amount of medication remaining in an IV bag) associated with the subject on the person support apparatus 10, the computer 104 may be configured and operable to determine, using data received from the at least one camera 102, status of the health monitor of status of a medication. For example, the computer 104 may be operable to determine whether the subject is experiencing a medical condition (i.e., whether a medical event is occurring) or whether the subject's health parameters are in a normal or healthy range, as indicated by the health monitor, and/or whether the subject is in need of a refill of medication (or whether the medication is being appropriate ingested by or administered/transmitted to the subject).

In some embodiments, the computer 104 is operable to determine how long the subject is on the person support apparatus 10 and identify instances where the subject leaves or exits the person support apparatus 10. The computer 104 may determine length of time that the subject is on the person support apparatus 10 and/or identify the absence of the subject from the person support apparatus 10 (e.g., the subject exiting/leaving the person support apparatus 10 or the subject falling off of the person support apparatus 10, etc.) via data from the at least one camera 102 and/or from data from the at least one sensor 112 (e.g., one or more pressure sensors positioned on the person support apparatus 10). In such embodiments, an alert may be output upon detecting that the subject has exited the person support apparatus 10 and/or has been absent from the person support apparatus 10 for more than a predetermined length of time. The alert may be output by the computer 104, and/or the computer 104 may generate and transmit the alert to or through one or more of the at least one handheld device 190 and the at least one remote station 192.

During use, the subject may turn, roll, or reposition themselves, and, in the process of doing so, the subject put themselves at risk of falling off of the person support surface 10, for example, by turning or rolling off of the person support surface 10. Thus, in some embodiments, the computer 104 is operable to identify movement of the subject on the person support apparatus 10 and/or proximity of the subject to edges of the person support apparatus 10 in order to detect instances where the subject is at risk of falling off of the person support apparatus 10. In these embodiments, the computer 104 may analyze image data received from the at least one camera 102 and/or data from the at least one sensor 112 (e.g., one or more pressure sensors positioned on the person support apparatus 10) to determine when the subject is moving (e.g., turning or rolling), the exact positioning or location of the subject on the person support surface 10, and/or how close the subject is to the edges of the person support apparatus 10. For example, the computer 104 may detect when the subject is within a predetermined distance from an edge of the person support apparatus 10, which would indicate that the subject is at risk of falling off of the person support apparatus 10, and then, if the computer 104 determines that the subject is within the predetermined distance from the edge of the person support apparatus 10, the computer 104 may generate an alert to warn the subject and/or a clinician that the subject is at risk of falling off of the person support surface 10. The computer 104 may generate and transmit the alert to or through one or more of the at least one handheld device 190 and the at least one remote station 192 upon determining that the subject is within the predetermined distance or otherwise at risk of falling off of the person support apparatus 10. In embodiments, when the computer 104 determines that the subject is within the predetermined distance or otherwise at risk of falling off of the person support apparatus 10, the computer 104 may control articulation of the articulating deck frame 22 (e.g., by sending a control signal to the articulating deck frame 22 instructing the articulating deck frame 22 to incline, decline, roll left, and/or roll right) to move the subject away from the edge of the person support apparatus 10, such that the subject is no longer at risk of falling. In these embodiments, the computer 104 may automatically cause repositioning of the subject such that the subject is no longer within the predetermined distance or otherwise at risk of falling off of the person support apparatus 10, or the computer 104 may notify the subject and/or the clinician of the risk and ask for permission before repositioning of the subject.

The computer readable and executable instructions 110 of the vision system 100 may include various types of algorithms or programs for performing various functions or features. For example, one or more algorithms may be stored in the memory 108 of the computer 104. The algorithms may pertain to video analytics for subject positioning, subject identification, identification of objects/items in the environment surrounding the subject, etc. In embodiments, the memory 108 storing the algorithms may be modular/removable to allow removal and replacement. In embodiments, the algorithms are stored on an external storage device (e.g., solid state external drive) that is communicatively coupled to the computer 104, for example, via an input port or USB port of the computer 104. In embodiments, the memory 108 is incorporated within the computer 104.

In embodiments, the vision system 100 is couplable to one or more cameras or camera systems external the vision system. For example, the computer 104 may be communicatively coupled to one or more other cameras in addition to the at least one camera 102. Such additional cameras may be wall or ceiling mounted, or mounted elsewhere in the room in proximity to the subject, and/or may be modular. For example, the computer 104 may be communicatively coupled to a camera located in a room within which the subject is located, such that the vision system 100 is able to keep track and monitor the subject even when they are not on the person support apparatus 10. In addition to observing the subject when they are not on/in the person support apparatus 10, such one or more other cameras may help facilitate calibration of the at least one camera 102, for example, due to changes in light. That is, the memory 108 may include an algorithm that calibrates the at least one camera 102 based on ambient light detected by the at least one camera 102, the at least one sensor, and/or the one or more other cameras. For example, the at least one sensor 112 may include one or more ambient light sensors, which may be coupled the person support apparatus 10 and/or elsewhere about the room within which the person support apparatus 10 is provided. Depending on the amount of ambient light in the room, as sensed by the one or more ambient light sensors, the computer 104 may adjust calibration of the at least one camera 102 to optimize the at least one camera 102 for use in that ambient light in which the at least one camera 102 is operating. Stated differently, the computer 104 may calibrate the at least one camera 102 based on ambient light data received from the at least one ambient light sensors. In another embodiment, a light emitter is provided that emits light at a known wave length that the ambient light sensor captures and the computer 104 calibrates the at least one camera 102 based on the light received from the light emitter.

In embodiments, the vision system 100 may include one or more security features. For example, the computer 104 may include mechanical locks and/or other devices to physically protect the components of the computer 104 from unauthorized third parties. Also, data stored on the vision system 100, for example, on the memory 108, may include password protection and/or encryption to safe guard data thereon from unauthorized access.

In embodiments, the vision system 100 may be configured to establish a network connection so as to communicate with one or more remote servers. For example, the computer 104 may communicate wireless or via a wired connection with one or more remote servers. In this manner, data from the at least one camera 102 and/or the at least one sensor 112 may be remotely streamed on a device/display associated with the remote server. Also, depending on the nature of the algorithm stored in the memory 108, the algorithm may generate output and such output may be monitored remotely on device/display associated with the remote server, as well as on the at least one handheld device 190 and the at least one remote station 192.

In embodiments, the vision system 100 is operable to automatically adjust or position the at least one camera 102 based on position of the subject. For example, the algorithm stored in the memory 108 may, when executed by the processor 106, control positioning of the field of view of the at least one camera 102 (and/or the angle at which the at least one camera 102 is oriented) based on feedback regarding the orientation or articulation of the articulating deck frame 22. With reference to FIGS. 1 and 2, the vision system 100 may be communicatively coupled to the control panel 38, such that the processor 106 receives the feedback regarding orientation or articulation of the articulating deck frame 22, the mattress head section 32, the mattress center section 36, and/or the mattress foot section 34 from the control panel 38 (or from a controller of the articulating deck frame 22) and utilizes such feedback to automatically adjust or position the at least one camera 102. In embodiments, the feedback is indicative of a position (e.g., a vertical spacing) of the articulating deck frame 22 relative to the base frame 16, an angle at which the mattress head section 32 is positioned relative to the mattress center section 36, and/or an angle at which the mattress foot section 34 is positioned relative to the mattress center section 36. For example, the control panel 38 is operable to adjust the articulating deck frame 22, the mattress head section 32, the mattress center section 36, and/or the mattress foot section 34, and the processor 106 is in communicate with the control panel 38 such that the computer 104 is operable to move the at least one camera 102 and adjust its field of view based on the position of the articulating deck frame 22, the mattress head section 32, the mattress center section 36, and/or the mattress foot section 34. In embodiments, the computer 104 is operable to calibrate the at least one camera 102 based on feedback from the control panel 38. For example, articulation of the person support apparatus 10 may result in a subject (and/or another object) being at least partially outside of the field of view of the at least one camera 102, and/or such movement of the person support apparatus 10 may result in the at least one camera 102 being out of focus, and the computer 104 may automatically move and/or focus the at least one camera 102 to ensure that the subject (and/or other objects) are within the field of view and/or within focus of the at least one camera 102. Thus, when the articulating deck frame 22 of the person support apparatus 10 inclines or declines, the processor 106 receives data indicative of the orientation of the articulating deck frame 22 from the control panel 38 and correspondingly adjusts position or orientation of the at least one camera 102 based on the same. In some of these embodiments or other in other embodiments, the at least one sensor 112 senses position of the subject and the processor 106 receives data therefrom indicative of the position of the subject and correspondingly adjusts position or orientation of the at least one camera 102 based on the position of the subject. In this manner, the at least one camera 102 may remain focused on the subject (or other object) regardless of movement (e.g., incline or decline) of the articulating deck frame 22.

In embodiments, the vision system 100 automatically repositions the at least one camera 102 based on optical feedback. For example, the algorithm stored in the memory 108 may cause the processor 106 to automatically adjust the field of view of the at least one camera 102 in cases where the subject (or other object) is nearing an edge or periphery of the field of view, to ensure that the subject (or other object) remains substantially centered or sufficiently within the field of view. In these embodiments, the algorithm is written such that the at least one camera 102 or other one or more of the at least one sensor 112 senses a position of the subject (or another object) and, as the subject (or other object) nears an edge or periphery of the field of view, as determined by data received from the at least one camera 102 and/or the at least one sensor 112, the processor 106 causes the at least one camera 102 to reposition based on feedback from the at least one camera 102 or the at least one sensor 112.

In embodiments, the vision system 100 may be associated with a particular person support apparatus 10. For example, a particular person support apparatus 10 may have a unique identifier and the unique identifier may be programmed into the computer 104 such that a user utilizing the vision system 100 will understand that the vision system is associated with the person support apparatus 10 having the particular unique identifier. In this manner, staff using the vision system 100 may know exactly which one of the person support apparatus 10 is being monitored, decreasing any chance of confusion as to which bed and/or subject is being monitored, as the vision system 100 is just associated with a single bed. Therefore, the vision system 100 is associated with the subject who is on the particular on of the person support apparatus 10. This may enable caregivers to track how long the subject is on the person support apparatus 10 and identify instances where the subject leaves or exits the person support apparatus 10. In other embodiments, the vision system 10 may be associated with more than one bed and/or more than one subject.

In embodiments, the memory 108 includes a facial recognition algorithm. In these embodiments, the facial recognition algorithm may associate a subject to the specific one of the person support apparatus 10 on which the at least one camera 102 is located. This may allow clinicians to identify which subjects are in which hospital rooms, and it may also provide a means to associate data from the bed to a subject. For example, where the person support apparatus 10 is capturing biometric data about the subject, such as heart rate, respiratory rate, weight, height, time that the subject spends on the person support apparatus 10, instances of when the subject exists/leaves the person support apparatus 10, etc., such data may be associated with the subject that was identified via the facial recognition algorithm located on the memory 108. Further, the vision system 100 may be communicatively coupled to an electronic medical record ("EMR") database, and such biometric data may be sent to the EMR associated with the subject and/or the subject's EMIR may be updated based on the biometric data.

In embodiments, the vision system 100 may also utilize indicators such as a bar code (or QR code) or a numerical designation that, when placed in the subject's room and within view of the at least one camera 102, causes the vision system 100 to recognize the person support apparatus 10 (on which the subject is placed) is located within a specific room. In embodiments, the bar code, QR code, numerical designation, or other type of indicator may be provided as a label. When utilized in combination with the facial recognition algorithm, the at least one camera 102 may capture an image of both the subject (i.e., the subject's face) and the bar code, and the processor 106 may identify the subject and the data on the bar code and then associate the subject with the data on the bar code. For example, the data on the bar code may be indicative of a particular room and/or a particular one of the person support apparatus 10, and then the processor 106 may then associate the recognized subject with the particular room and/or the particular one of the person support apparatus 10 indicated on the bar code. Where utilized, a bar code may be provided on a sticker, and the sticker with the bar code may be placed on the person support apparatus 10 or on a wall (or piece of furniture) that is in the field of view of the at least one camera 102. Further, a central computer system of the hospital may be communicatively coupled with the vision system 100 and track location of the vision system 100 and/or the person support apparatus 10 associated therewith wherever it is located (e.g., within the hospital), such that the central computer system may thereby track location of the subject that is associated with the vision system 100 and/or the person support apparatus 10. This may enable caregivers to track the subject throughout the hospital, for example, in scenarios where the subject leaves or exits the bed. For example, the vision system 100 may enable tracking how long the subject is (or has been) positioned on the person support apparatus 10. In some examples, the person support apparatus 10 is in a single room, and the vision system 100 may enable tracking how the subject has been in that particular room. For example, the room may be associated with a certain service or certain type of care, such that the vision system 100 is operable to track how long the subject has been undergoing that type of service of care.

Figure 3A:
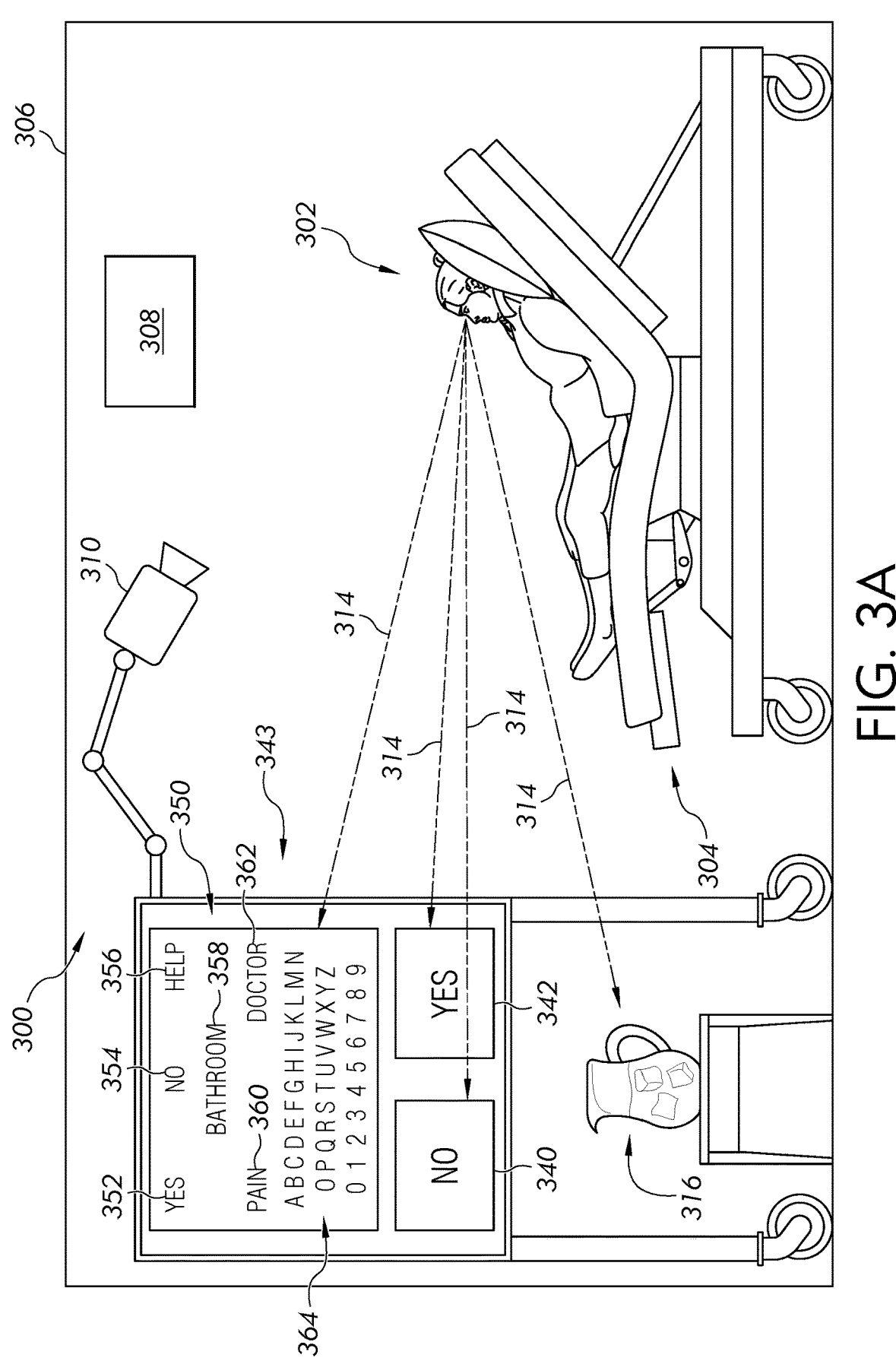
FIG. 3A schematically depicts a vision system for facilitating communication with a subject, according to one or more embodiments.
Figure 4A:
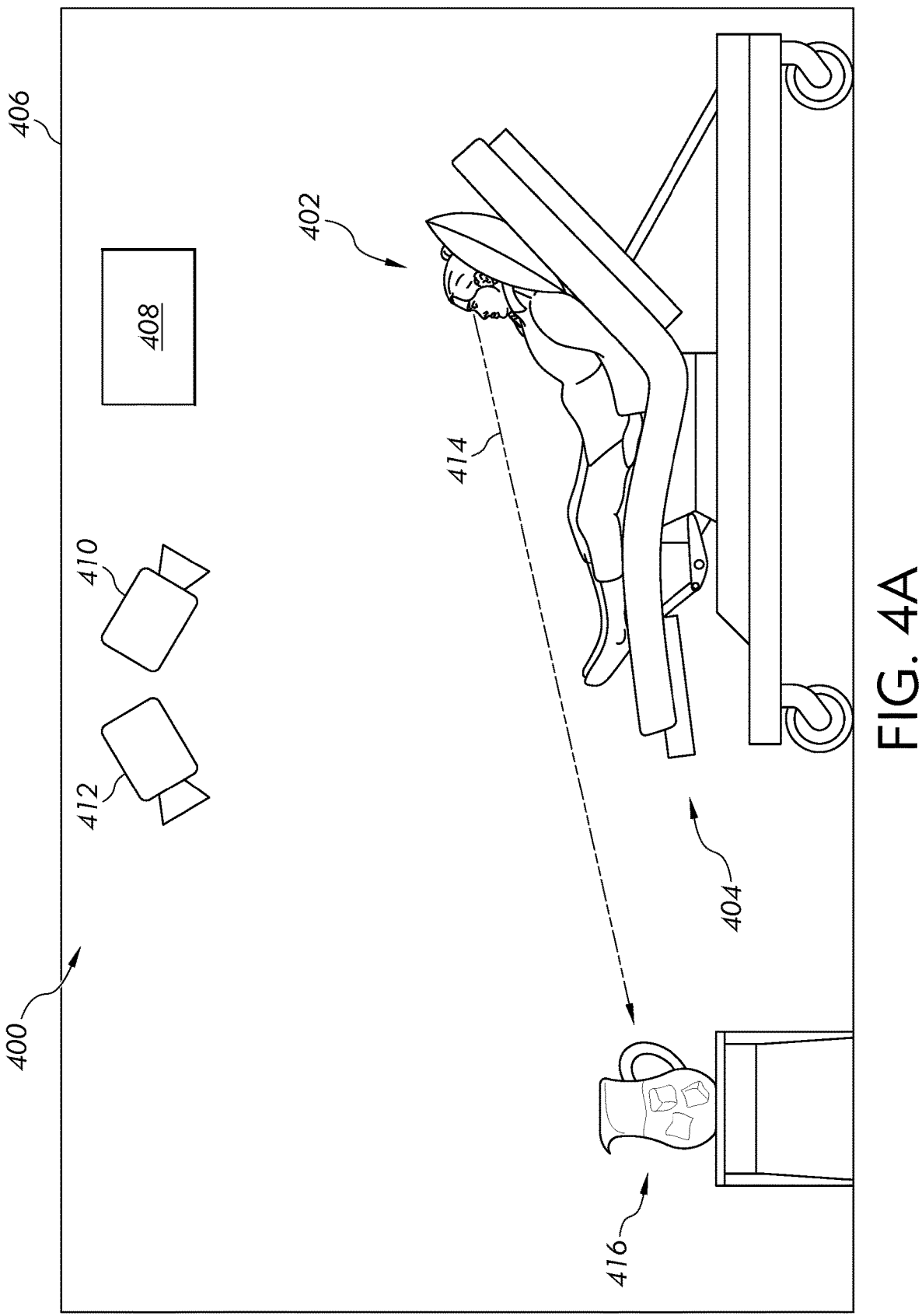
FIG. 4A schematically depicts another vision system for facilitating communication with a subject, according to one or more embodiment.
Figure 5A:
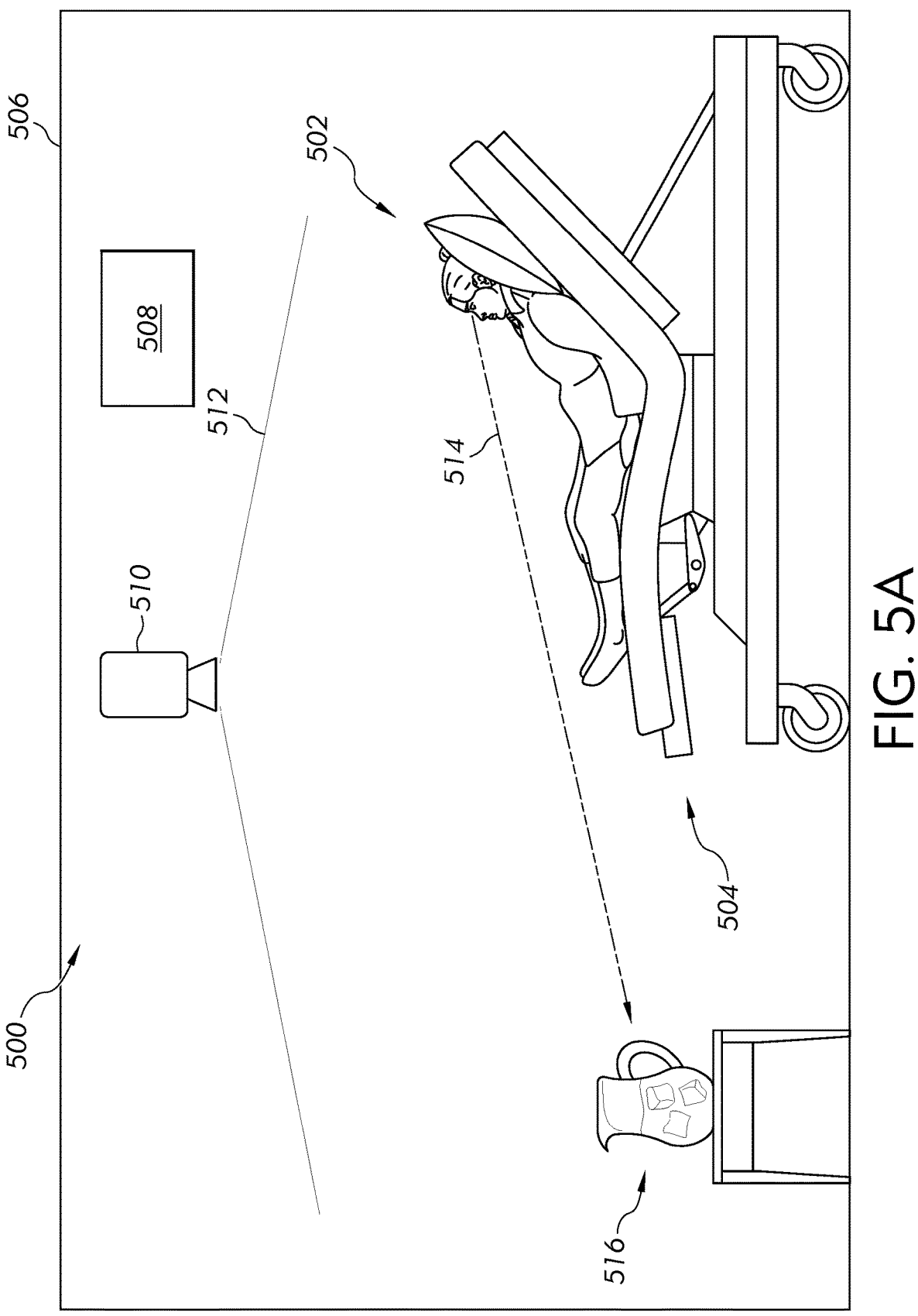
FIG. 5A schematically depicts yet another vision system for facilitating communication with a subject, according to one or more embodiment.

In some clinical situations, subjects may be immobile and/or not have an ability to communicate verbally or through physical movements (i.e., gesturing). In these situations, subjects may need some form of aid or assistance (e.g. they need water, are in pain, they need a position change, etc.) which may not be recognized by the clinical staff. FIGS. 3A, 4A, and 5A illustrate example vision systems that may be utilized to facilitate communication with subjects.

FIG. 3A illustrates a vision system 300 utilized to facilitate communication with a subject 302, according to one or more embodiments. As shown, the subject 302 is positioned on a bed 304, and the bed 304 is located within a room 306. The bed 304 may be provided similar as described above with reference to the person support surface 14. In the illustrated embodiment, vision system 300 includes a computer 308 and a camera 310 in communication with the computer 308. The computer 308 may be provided similar as described above with reference to the computer 104. The computer 308 and the camera 310 may be in communication via a cable/cord or via wireless communication.

The camera 310 is focused on the subject 302 (e.g., the eyes of the subject 302) and an algorithm is stored in the computer 308 that enables the computer 308 to identify or calculate a gaze direction 314 that the subject 302 is looking (i.e., gazing or staring). Also, the location of one or more objects 316 may be stored in the computer 308. The computer 308 is able to correlate the gaze direction 314 with the one or more objects 316. For example, a coordinate system may be associated with the room 306 and the one or more objects 316 may be associated with a specification position (e.g., a set of coordinates) within the coordinate system, and the computer 308 may associate the gaze direction 314 as a vector and correlate the vector of the gaze direction 314 with a location in the room. If the gaze direction 314 is indicative of a location in the area 306 that is the same as the preprogrammed location of the one or more objects 316 (i.e., if the gaze direction 314 aligns with or is correlated with the preprogrammed location of the one or more objects 316), then the computer 308 determines that the subject 302 is communicating about the one or more objects 316 and the computer 308 may output a notification. In the illustrated example, the one or more objects 316 is a pitcher of water, and the computer 308 is programmed to associate the pitcher of water with a communication from the subject 302 indicating that the subject 302 wants water. The vision system 300 may then output a notification to communicate this message to caregivers in a variety of manners. For example, the vision system 300 may include one or more speakers and output the message as an audible message stating "I want water", and/or the vision system 300 may include one or more monitors (e.g., such as the at least one handheld device 190 and the at least one remote station 192) on which the message is textually displaced and such one or more monitors may be provided in the room 306 and/or in another remote location. Because the vision system 300 utilizes a single camera (i.e., the camera 310) and does not necessarily include feedback (i.e., position feedback) from another camera, it may be considered an open-loop feedback system.

In embodiments, the one or more objects 316 includes a pair of signs, such as a first sign 340 that reads "No" and a second sign 342 that reads "yes". In these examples, the caregiver may ask the subject 302 questions, and the subject 302 may respond by looking at either the "no" sign or the "yes" sign. In embodiments, the location of both signs are stored in the computer 308 and, when the gaze direction 314 aligns with the preprogrammed location of either sign, the computer 308 is able to determine whether the subject 302 is staring at the "no" sign or the "yes" sign, and alert the caregiver as to the same. In other embodiments, the "no" sign and the "yes" sign may each be spaced at a known distance from the subject 302 and may be positioned apart from each other at a known distance, such that a triangle is defined between the subject 302, the "no" sign, and the "yes" sign, and the length of each leg of the triangle is known and stored in the computer 308. When the subject 302 stars at either the "no" sign or the "yes" sign, the computer 308 is able to calculate the angle at which the eyes of the subject 302 are directed and, if the angle at which the subject 302 is staring correlates with either the "no" sign or the "yes" sign, the computer 308 may alert the caregiver as to the same. For example, when looking at the "no sign", the gaze direction 314 of the subject 302 may be oriented at minus forty five degrees (−45°) from a center line and, when looking at the "yes sign", the gaze direction 314 of the subject 302 may be oriented at plus forty five degrees (+45°) from a center line, and the computer 308 may be programmed to associate "no" with (−45°) and "yes" with (+45°). In these examples, the caregiver could ask the subject 302 a "yes" or "no" question and then direct the subject 302 to answer by looking either the "no" sign or the "yes" (or another of the one or more objects 316). Also, while the foregoing examples describe just two signs reading "yes" and "no", more or less signs having any number of different content or communication may be utilized using these principles. In embodiments, the signs 340, 342 are mounted on a mobile cart 343, such that they may be maneuvered or repositioned within the room 306. In embodiments, the camera 310 and the computer 308 are also disposed on the mobile cart 343, such that the camera 310, the computer 308 may be maneuvered or repositioned within the room 306. For example, the mobile cart 343 may be moved into close proximity with the bed 304 such that the subject is able to view the content contained on the signs 340, 342. In embodiments where the camera 310 is disposed on the mobile cart 343, the camera 310 may be coupled to the mobile cart 343 via a boom, as described with reference to the boom 70 in FIG. 1.

In other embodiments, the one or more objects 316 includes a board 350 with a plurality of images or phrases, and the subject may communicate the content of the items or phrases to the caregiver by gazing at the items or phrases. In the illustrated embodiment, the board 350 includes phrases 352, 354, 356, 358, 360, 362, each of which may be associated with a specification position (e.g., a set of coordinates) within the coordinate system. Also in the illustrated embodiment, the board 350 includes an alphabet and numbers 364, each of which may be associated with a specification position (e.g., a set of coordinates) within the coordinate system. Here, the specific position of each of the phrases 352, 354, 356, 358, 360, 362 and the alphabet and numbers 364 is stored in the computer 308, and the computer 308 is operable to associate the gaze direction 314 as a vector and correlate the vector of the gaze direction 314 as being directed towards any one of the phrases 352, 354, 356, 358, 360, 362 or towards any particular letter or number in the alphabet and numbers 364 presented on the board 350. Then, if the computer 308 determines that the subject 302 looking at any one of the phrases 352, 354, 356, 358, 360, 362, or at any particular letter or number in the alphabet and numbers 364, which indicates that the subject 302 is attempting to communicate that particular phrase or letter/number, the computer 308 may output a notification indicative of the same. In the illustrated embodiment, the phrases 352, 354, 356, 358, 360, 362 correspond with "yes," "no," "help," "bathroom," "pain," and "doctor"; however, more or less phrases may be used in addition to or instead of the foregoing, and/or one or more images or other types of means of communication may be utilized in addition to or in lieu thereof. Also, while the alphabet and numbers 364 corresponds to the English alphabet and numbers 0 to 9, other alphabets or number systems may be utilized in addition to or in lieu thereof. Also, various types of symbols may be presented on the board 350, such as mathematical operation symbols, punctuation symbols, etc., thereby enhancing the subject's 302 ability to communicate various types of information. In embodiments, the computer 308 is programmed to recognize facial expressions and/or gestures of the subject that are indicative of the subject's desire.

In embodiments, the board 350 is a display screen that is connected to a computer and operable to present various messages, images, etc. as determined by the computer to which it is connected. In some of these embodiments, the board 350 is connected to the computer 308 and the computer 308 is configured to cause the board 350 to display various messages, images, etc., such as the phrases 352, 354, 356, 358, 360, 362 and/or the alphabet and numbers 364. Here, the computer 308 causes the phrases 352, 354, 356, 358, 360, 362 and/or the alphabet and numbers 364 to be displayed on the board 350 at certain locations thereon, such that the computer 308 knows the location at which the phrases 352, 354, 356, 358, 360, 362 and/or the alphabet and numbers 364 are presented on the board 350 and, if the computer 308 determines that the subject 302 looking at any one of the phrases 352, 354, 356, 358, 360, 362 and/or the alphabet and numbers 364, the computer 308 is configured to output a notification indicative of the same.

In embodiments, the board 350 is mounted on the mobile cart 343. In this manner, the board 350 may be maneuvered or repositioned within the room 306. In embodiments, the camera 310 and the computer 308 are also disposed on the mobile cart 343, such that the camera 310 and the computer 308 may be maneuvered or repositioned within the room 306 with the board 350. Accordingly, the vision system 300 may be maneuvered within the room 306 and moved relative to the bed 304, such that the vision system 300 may be moved out of the way so as to not create an obstacle within the room 306, for example, when not being utilized, and/or the vision system 300 may be moved as close to the bed 304 as may be desired depending on the subject 302 in the bed and their ability to see the signs 340, 340 and the board 350.

Figure 3B:
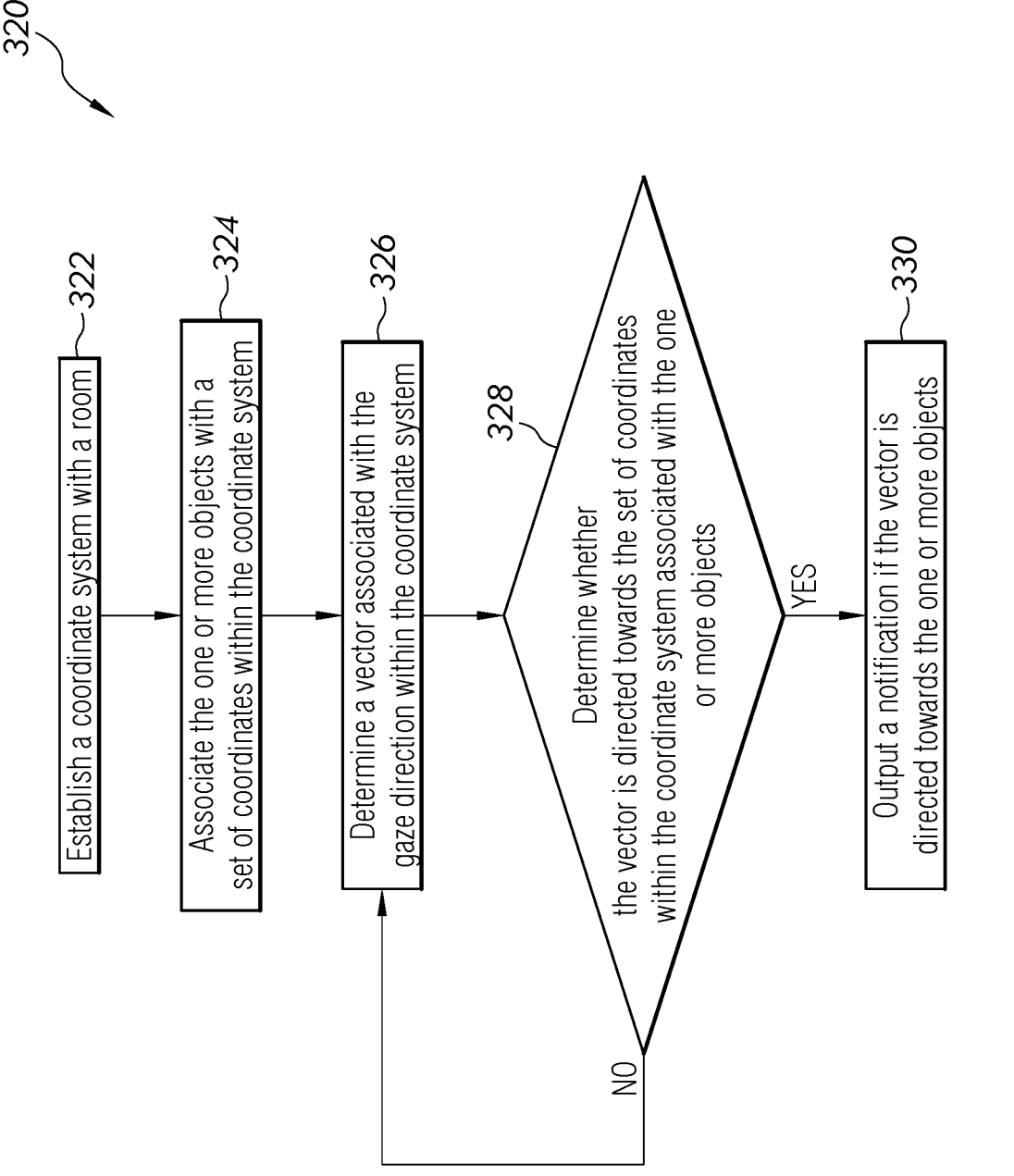
FIG. 3B is a flow diagram of an example method of facilitating communication with a subject using the vision system of 3A, according to one or more embodiments.

FIG. 3B illustrates a method 320 of facilitating communication with the subject 302 utilizing the vision system 300, according to one or more embodiments. At block 322, a coordinate system is established for the room 306. In embodiments, the user may manually establish the coordinate system and store it in the computer 308, or one or more scanners or cameras coupled to the computer 308 may scan the room 306 and automatically generate the coordinate system corresponding with the room 306 and store it in the computer 308. At block 324, the one or more objects 316 are associated with a set of coordinates in the coordinate system that was previously established for the room 306 at block 322. In embodiments, the user may manually associate the one or more objects 316 with the set of coordinates, or the computer 308 may scan the room 306 and automatically generate the set of coordinates with in the coordinate system for the one or more objects 316. At block 326, the computer 308 determines a vector of the gaze direction 314. Here, the camera 310 is focused on the subject 302 and recording the subject 302, and the computer 308, which is communicably coupled to the camera 310, is able to calculate the vector based on data received from the camera 310. At block 328, the computer 308 determines whether the vector is directed towards the set of coordinates within the coordinate system associated with the one or more objects 316. Here, the computer 308 may map the vector in the coordinate system established for the room 306 and determine if the vector extends to the one or more objects 316. If the computer 308 determines that the vector is directed towards the one or more objects 316 (i.e., "yes"), then a notification is output indicating that the subject 302 is looking at the one or more objects 316, as indicated at block 330. If the computer 308 determines that the vector is not directed towards the one or more objects 316 (i.e., "no"), then the vision system 300 continues to monitor the subject 302 and continues to determine the vector of the gaze direction 314 of the subject 302.

FIG. 4A illustrates another vision system 400 including a plurality of cameras utilized to facilitate communication with a subject 402, according to one or more embodiments. As shown, the subject 402 is positioned on a bed 404, and the bed 404 is located within a room 406. The bed 404 may be provided similar as described above with reference to the person support surface 14. In the illustrated embodiment, In the illustrated embodiment, vision system 400 includes a computer 408, a first camera 410, and a second camera 412, wherein both the first camera 410 and the second camera 412 are in communication with the computer 408. The first camera 410 and the second camera 412 may be in communication with the computer 408 via a cable/cord or via wireless communication. The computer 408 may be provided similar as described above with reference to the computer 104.

As shown, the first camera 410 is focused on the subject 402 (e.g., the eyes of the subject 402) and an algorithm is stored in the computer 408 that enables the computer 408 to identify or calculate a gaze direction 414 that the subject 402 is looking (i.e., gazing or staring). Also in the illustrated embodiment, the second camera 412 is focused on one or more objects 416, and the algorithm stored in the computer 408 enables the computer 408 to determine if the gaze direction 414 of the subject 402, as captured by the first camera 410, corresponds to (i.e., is directed at) the one or more objects 416. Thus, the vision system 400 is able to determine the desired communication of the subject 402 focusing the first camera 410 on the subject 402 to identify the gaze direction 414 and to correlate that gaze direction with the one or more objects 416 contained in the field of view of the second camera 412. In embodiments, the vision system 400 includes one or more additional cameras, in addition to the first camera 410 and the second camera 412, with such additional cameras focused on other areas within the room 406 such that the subject 402 may look at any location in the room 406 and that location may be identified via the second camera 412 and/or any one or more of the additional cameras.

In these embodiments, the computer 408 may include an algorithm that identifies the gaze direction 414 of the user based on data captured by the first camera 410. The algorithm may also determine whether the gaze direction 414 of the subject is associated with the one or more objects 416 contained in the field of view of the second camera 412.

In the illustrated example, the one or more objects 416 is a pitcher of water, and the computer 408 is programmed to associate the pitcher of water with a communication from the subject 402 that they want water. In embodiments, the one or more objects 416 may be different. For example, the one or more objects 316 may include a one or more signs having various symbols, text, illustrations, etc. The sign may also utilize QR codes, bar codes, or other means by which the vision system 400 may identify the message. The vision system 400 may also be trained to recognize the image as seen by the subject 402 and convert the image to the appropriate request to be relayed to a caregiver. Utilization of QR codes and/or bar codes may be useful in cases where the vision algorithm was not yet trained to recognize the one or more objects 416. For example, a container of water may take on many shapes/forms and, in some cases, it may be easier to attach a label with a QR code or bar code (or other type of non-human readable sticker) to the one or more objects 416 for object identification and training, rather than to train the algorithm on all possible permutations of the one or more objects 416.

In other embodiments, the one or more objects 416 may include a board with one or more phrases or images presented thereon, as described with reference to the signs 340, 342 and/or the board 350 in FIG. 3A. In such embodiments, the computer 408 is programmed to identify the gaze direction 414 of the user based on data captured by the first camera 410 and the computer 408 is programmed to determine whether the gaze direction 414 of the subject is associated with a particular phrase or image presented on the board(s) contained in the field of view of the second camera 412, and thereafter output a notification indicating that the gaze direction 414 corresponds with the phrase or image presented on the board.

Because the vision system 400 utilizes more than one camera (i.e., first camera 410 and the second camera 412) and uses position information from the second camera 412 that is fed back into the vision system 400 (i.e., as position feedback) to correlate the gaze direction 414 with the one or more objects 416, it may be considered a closed-loop feedback system.

Figure 4B:
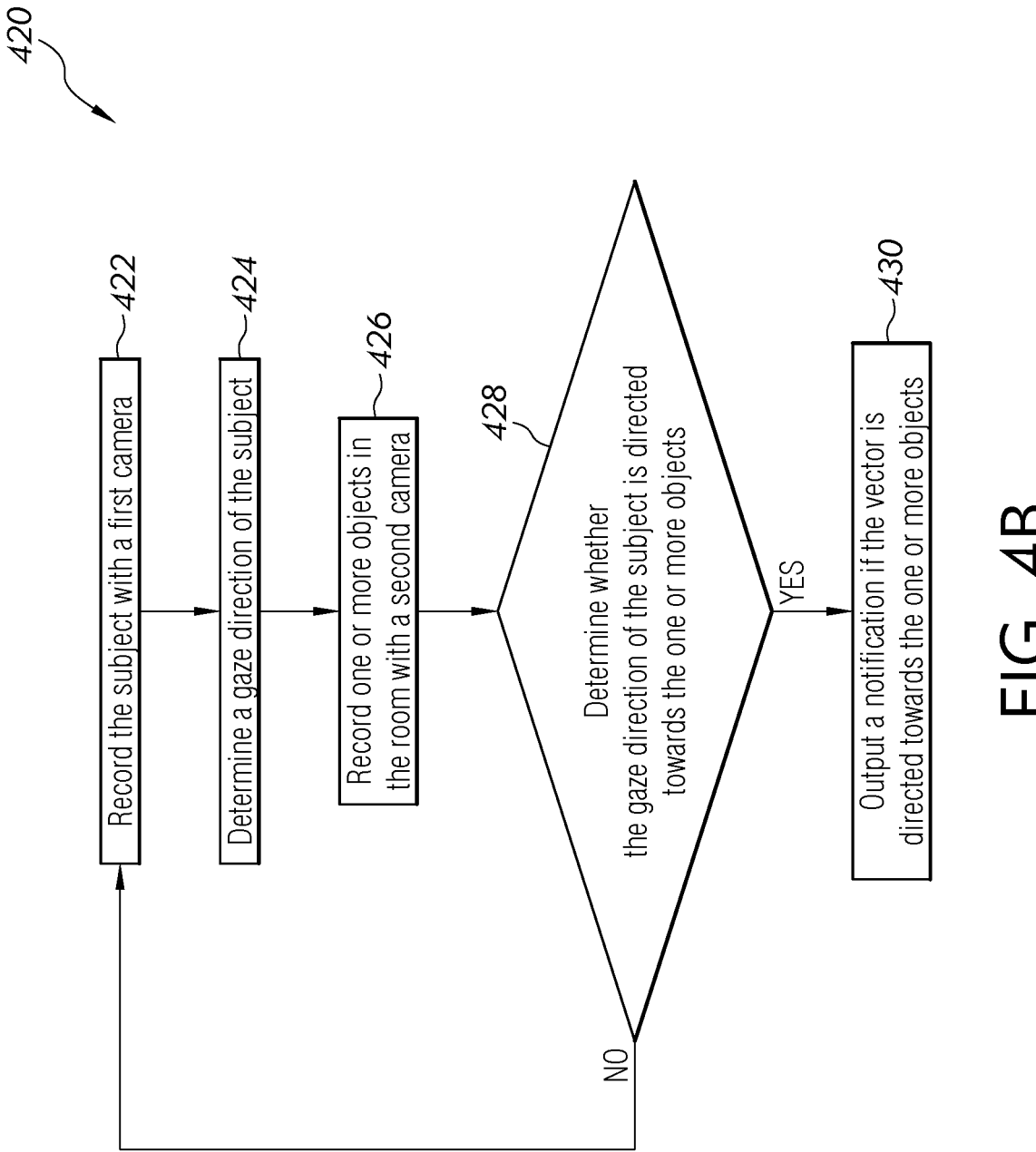
FIG. 4B is a flow diagram of an example method of facilitating communication with a subject using the vision system of 4A, according to one or more embodiments.

FIG. 4B illustrates another method 420 of facilitating communication with the subject 402 utilizing the vision system 400, according to one or more embodiments. At block 422, the subject 402 is recorded with the first camera 410 and, at block 424, the computer 408 determines a gaze direction 414 of the subject 402. Here, the field of view of the first camera 410 contains the subject 402 and the computer 408, which is communicably coupled to the first camera 410, is programmed to determine the gaze direction 414 of the subject 402 based on positioning of the eyes as sensed by the first camera 410. At block 426, the one or more objects 416 are recorded by the second camera 412. The one or more objects 416 may include an individual object or sign in the room 406, or may include a plurality of objects/signs positioned throughout the room 406. At block 428, the computer 408 determines whether the gaze direction 414 of the subject 402 is directed towards the one or more objects 416 captured by the second camera 412. Here, the computer 408 may map the gaze direction 414 into the image of the room 406 captured by the second camera 412 to thereby determine if the gaze direction 414 of the subject 402 points towards any particular one of the one or more objects 416. If the computer 408 determines that the gaze direction 414 is directed towards the one or more objects 416 (i.e., "yes"), then a notification is output indicating that the subject 402 is looking at the one or more objects 416, as indicated at block 430. If the computer 408 determines that the gaze direction 414 of the subject 402 is not directed towards the one or more objects 416 (i.e., "no"), then the vision system 400 continues to monitor the subject 402 with the first camera 410 and continues to determine the gaze direction 414 of the subject 402, as indicated at block 422.

FIG. 5A illustrates yet another vision system 500 utilized to facilitate communication with a subject 502, according to one or more embodiments. As shown, the subject 502 is positioned on a bed 504, and the bed 504 is located within a room 506. The bed 504 may be provided similar as described above with reference to the person support surface 14. In the illustrated embodiment, the vision system 500 includes a computer 508 and a camera 510 that is in communication with the computer 508. The camera 510 and the computer 508 may be in communication with each other via a cable/cord or via wireless communication. The computer 508 may be provided similar as described above with reference to the computer 104.

In the illustrated embodiment, the camera 510 is a wide-angle optic camera capable of simultaneously capturing in its field of view 512 both a gaze direction 514 of the subject 502 and one or more objects 516. An algorithm may be programmed into the computer 508 that operates in a similar fashion as described with regard to the vision system 400 of FIG. 4A, except that the vision system 500 of FIG. 5A utilizes an individual camera rather than a pair of cameras. For example, the field of view of the camera 510 simultaneously contains the subject 502 and the one or more objects 516, and the computer 508 calculates the gaze direction 514 that the subject 502 is looking (i.e., gazing or staring) and determines whether the gaze direction 514 corresponds to (i.e., is directed at) the one or more objects 516. In these embodiments, the algorithm may be programmed to account for any image distortion that may occur when using wide-angle lenses and, therefore, the algorithm may be programmed to correct any distortions that may occur with the viewing of the subject 502 and/or the one or more objects 516.

As described with reference to the board 350 in FIG. 3A above, the one or more objects 316,416,516 may be a digital display that outputs one or more options as determined by the vision system 300,400,500. For example, the computer 308, 408, 508 may be communicatively coupled to the digital display and be programmed to output some sort of message or communication to the subject 302, 402, 502, and a question may be presented on the digital display with one or more programmed answers from which the subject 302, 402, 502 may select. When the subject 302, 402, 502 looks at a particular answer to select that particular answer, the gaze direction 314, 414, 514 is directed at the particular answer and the computer 308, 408, 508 may determine which of the particular answers it was that the subject 302, 402, 502 was trying to communicate. The answers/messages presented on the digital display may be a plurality of commonly used answers/messages, or may be a customizable by the caregiver. In embodiments, the digital display presents an option to call one or more particular caregivers/ clinicians, and the subject 302, 402, 502 may look at an icon associated with the one or more particular caregivers/clinicians to call for their assistance.

Figure 5B:
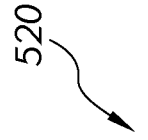
FIG. 5B is a flow diagram of an example method of facilitating communication with a subject using the vision system of 5A, according to one or more embodiments.
Figure 5B:
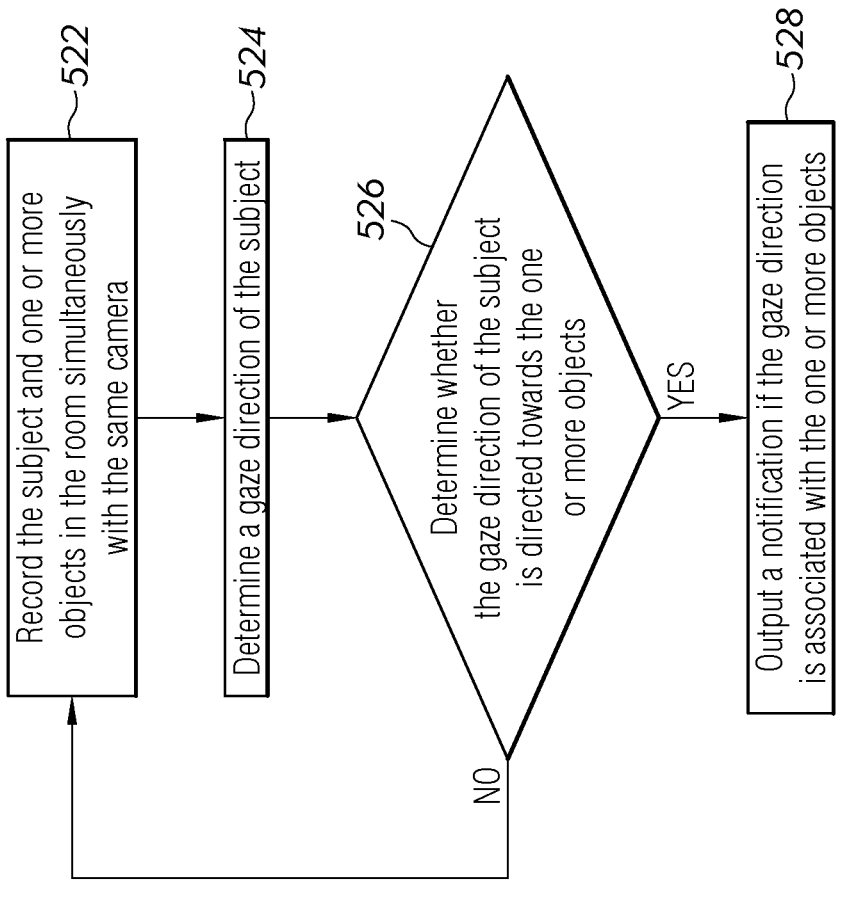

FIG. 5B illustrates yet another method 520 of facilitating communication with the subject 502 utilizing the vision system 500, according to one or more embodiments. At block 522, the subject 502 and the one or more objects 516 in the room 506 are simultaneously recorded with the (same) camera 510. While the vision system 500 is simultaneously monitoring the subject 502 and the room 506 via the camera 510, the computer 508 determines a gaze direction 514 of the subject 502 at block 524. At block 526, the computer 508 determines whether the gaze direction 514 of the subject 502 is directed towards the one or more objects 516. Here, the computer 408 may map the gaze direction 514 into the image of the room 506 to thereby determine if the gaze direction 514 of the subject 502 points towards any particular one of the one or more objects 516. If the computer 508 determines that the gaze direction 514 is directed towards the one or more objects 516 (i.e., "yes"), then a notification is output indicating that the subject 502 is looking at the one or more objects 516, as indicated at block 528. If the computer 508 determines that the gaze direction 514 of the subject 502 is not directed towards the one or more objects 516 (i.e., "no"), then the vision system 500 continues to monitor the subject 502 and the one or more objects 516 with the camera 510 and continues to determine the gaze direction 514 of the subject 502, as indicated at block 522.

It should now be understood that embodiments described herein are directed to vision systems for person support apparatuses and methods for utilizing vision systems to optimize care of a subject on or assigned to the person support apparatus. The vision systems described herein are mobile and easily maneuverable such that they be repositioned as may be desired so that they do not create or present an obstruction in the room within which the person support apparatus is provided and such that they may be moved closer to the subject or further from the subject, as may be desired. The camera of the vision systems described herein is modular, such that it may be moved to different mounting locations and, the camera is obscurable or camouflageable such that the camera is not readily apparent to the subject so as to reduce anxiety. The camera may be automatically or manually movable to adjust a field of view of the camera, or the computer may be operable to move the camera or adjust the field of view of the camera, such that the field of view of the camera contains the subject and/or the object that is intended to be contained therein. The vision system includes a computer and enhances communication with the subject, because the computer is configured determine where the subject is looking, so as to provide a means of non-verbal communication with the subject based on where the subject is looking. Vision systems described herein also facilitate tracking subjects, for example, by tracking how long the subject has been in a particular room, how long the subject has been on a particular bed, and/or whether the subject has left the bed and/or the room. Vision systems described herein provide a solution for facilitating communication between subjects and third parties (such as caregivers) and monitoring subjects, without cluttering space within which the subject is located.

Further aspects of the embodiments described herein are provided by the subject matter of the following clauses:

Clause 1. A vision system comprising: at least one camera positioned such that a field of view of the at least one camera contains a person support apparatus supporting a subject positioned thereon; and a computer communicatively coupled to the at least one camera, the computer configured to receive at least one image from the at least one camera and determine a tidal volume of the subject positioned on the person support surface from the at least one image.

Clause 2. The vision system of clause 1, wherein the at least one camera is positioned such that the field of view captures a health monitor associated with the person support apparatus, and the computer is further configured to determine, using data received from the at least one camera, status of health parameters and/or occurrence of a medical event as indicated by the health monitor.

Clause 3. The vision system of any one of clauses 1 to 2, wherein the at least one camera is positioned such that the field of view captures a medication associated with the person support apparatus, and the computer is further operable to determine, using data received from the at least one camera, whether the medication needs to be refilled and/or is being administered.

Clause 4. vision system of any one of clauses 1 to 3, wherein the at least one camera is a LIDAR camera.

Clause 5. The vision system of any one of clauses 1 to 4, wherein the person support apparatus comprises a plurality of mounting sites for mounting the at least one camera, and the at least one camera is mountable to the person support apparatus at any of the one or more of the mounting sites.

Clause 6. The vision system of any one of clauses 1 to 5, wherein the computer is further operable to store an algorithm therein for determining a gaze of the subject, determining that a target of the gaze of the subject corresponds to a location of an object, and outputting a notification indicating that the subject is viewing the object Clause 7. The vision system of any one of clauses 1 to 5, wherein the at least one camera includes a first camera focused on the person support apparatus and a second camera focused on an object, the computer being operatively connected to both the first camera and the second camera, the computer operable to store an algorithm therein for determining a gaze of a subject via the first camera, determining that a target of the gaze of the subject corresponds with a location of the object monitored by the second camera, and outputting a notification indicating that the subject is viewing the object.

Clause 8. The vision system of any one of clauses 1 to 5, wherein the at least one camera is positioned such that the field of view captures both the person support apparatus and an object, the computer is operable to store an algorithm therein for determining a gaze of a subject, determining that a target of gaze of the subject corresponds with a location of the object monitored by the at least one camera, and outputting a notification indicating that the subject is viewing the object.

Clause 9. The vision system of any one of clauses 1 to 8, further comprising a boom coupled to the at least one camera.

Clause 10. The vision system of clause 9, wherein the person support apparatus comprises a head end and a foot end, and the boom comprises a first ends disposed on the head end and a second end coupled to the at least one camera.

Clause 11. The vision system of any one of clauses 9-10, wherein the boom includes a plurality of linkage arms interconnected and coupled to each other via a plurality of rotational joints, and the at least one camera is supported on a distal most linkage arm of the plurality of linkage arms.

Clause 12. The vision system of clause 11, wherein one or more of the plurality of rotational joints are motorized rotational joints and communicatively coupled to the computer, wherein the computer is further operable to instruct actuation of the motorized rotational joints to rotate one or more of the plurality of linkage arms to move the positioning of the at least one camera to adjust the field of view.

Clause 13. The vision system of clause 12, wherein the person support apparatus comprises an articulating deck frame and a controller communicatively coupled to the articulating deck frame, the controller being operable to instruct actuation of actuators that articulate the articulating deck frame and thereby incline or decline a person support surface of the person support apparatus, and the computer is further communicatively coupled to the controller and operable to instruct actuation of the one or more of the motorized rotational joints to thereby adjust the field of view of the at least one camera based on data received from the controller.

Clause 14. The vision system of any one of clauses 1-13, further including at least one remote station communicatively coupled to the computer, the at least one remote station comprising at least one display for viewing an image from the field of view of the at least one camera.

Clause 15. The vision system of clause 14, wherein the at least one remote station is operable to control operation of the vision system.

Clause 16. The vision system of any one of clauses 14-15, further including a mobile cart, wherein the remote station is provided in the mobile cart.

Clause 17. The vision system of clause 16, wherein the at least one camera is supported on the mobile cart.

Clause 18. The vision system of clause 17, further including a boom that couples the at least one camera to the mobile cart.

Clause 19. The vision system of clause 18, wherein the boom includes a plurality of linkage arms interconnected and coupled to each other via a plurality of rotational joints, and the at least one camera is supported on a distal most linkage arm of the plurality of linkage arms.

Clause 20. The vision system of any one of clauses 1-13, wherein the computer is integrated within the person support apparatus or is provided external to the person support apparatus.

Clause 21. The vision system of any one of clauses 1-20, wherein the at least one camera is positioned such that the field of view thereof contains an indicator, the indicator being associated with a particular physical location, wherein the computer is configured to associate the person support apparatus with the particular physical location upon identification of the indicator.

Clause 22. A vision system comprising: a first camera positioned such that a field of view of the first camera contains a person support apparatus supporting a subject positioned therein; a second camera positioned such a field of view of the second camera contains an object therein; and a computer communicatively coupled to the first camera and the second camera, the computer configured to: receive at least one image from the first camera and determine a gaze direction of a subject from the at least one image from the first camera, receive at least one image from the second camera and determine a location of the object, determine whether the subject is looking at the object based on the gaze direction of the subject and the location of the object, and output a notification when the of the subject is looking at the object.

Clause 23. The vision system of clause 22, further including a board, wherein the object is presented on the board.

Clause 24. The vision system of clause 23, wherein the board is a digital display communicatively coupled to the computer, and the computer is configured to present information on the digital screen and determine whether the subject is looking at the information presented on the digital screen.

Clause 25. The vision system of any one of clauses 22-24, further including comprising a mobile cart, wherein the computer and the board are disposed on the mobile cart.

Clause 26. The vision system of clause 25, wherein the first camera and the second camera are disposed on the mobile cart.

Clause 27. The vision system of clause 26, further including a first boom that couples the first camera to the mobile cart and a second boom that couples the second camera to the mobile cart.

Clause 28. The vision system of clause 27, wherein the first boom and the second boom each includes a plurality of linkage arms interconnected and coupled to each other via a plurality of rotational joints, and the first camera and the second camera are each supported on a distal most linkage arm of the plurality of linkage arms.

Clause 29. A vision system for a person support apparatus, the vision system including: at least one camera positioned such that a field of view of the at least one camera contains both an object and the person support apparatus supporting a subject positioned therein; and a computer communicatively coupled to the at least one camera, wherein the computer is configured to: receive at least one image from the at least one camera and determine a gaze direction of the subject and a location of the object from the at least one image from the first camera; determine whether the subject is looking at the object based on the gaze direction of the subject and the location of the object; and output a notification when of the subject is looking at the object.

Clause 30. The vision system of clause 29, further including a mobile cart, and the computer and the at least one camera are disposed on the mobile cart.

Clause 31. The vision system of clause 30, further including a boom that couples the at least one camera to the mobile cart.

Clause 32. The vision system of clause 31, wherein the boom includes a plurality of linkage arms interconnected and coupled to each other via a plurality of rotational joints, and the at least one camera is supported on a distal most linkage arm of the plurality of linkage arms.

Clause 33. A method of determining tidal volume of a subject on a person support apparatus, the method including: receiving, at a computer, image data from a camera communicatively coupled to the computer, wherein the camera is positioned such that a field of view of the camera contains a display of a health monitor associated with the subject and the image data is indicative the tidal volume of the subject presented on the display of the health monitor; determining, via the computer, the tidal volume of the subject positioned on the person support surface based on the image data received from the camera; and outputting the tidal volume of the subject.

Clause 34. The method of clause 33, further including determining, via the computer, occurrence of a medical event involving the subject based on the image data.

Clause 35. The method of any one of clauses 33 to 34, wherein the field of view contains a medication being administered to the subject supported by the person support surface, and the method further includes: determining, via the computer, whether to refill the medication based on the image data.

Clause 36. The method of any one of clauses 33 to 35, wherein the field of view contains a medication being administered to the subject supported by the person support surface, and the method further includes: determining, via the computer, whether the medication is being administered to the subject based on the image data.

Clause 37. The method of any one of clauses 33 to 36, wherein the camera is attached to the person support apparatus.

Clause 38. The method of any one of clauses 33 to 36, further including a mobile cart, wherein the camera and the computer are provided in the mobile cart.

Clause 39. The method of any one of clauses 33 to 36, further including at least one remote station communicatively coupled to the computer, the at least one remote station comprising at least one display for viewing the tidal volume of the subject.

Clause 40. The method of clause 39, wherein outputting the tidal volume of the subject comprises outputting the tidal volume at the remote station.

Clause 41. A vision system comprising: at least one camera positioned such that a field of view of the at least one camera contains a person support apparatus supporting a subject positioned thereon; and a computer communicatively coupled to the at least one camera, the computer configured to receive at least one image from the at least one camera, determine whether the subject is present on the person support surface from the at least one image, and generate an alert indicating that the subject is not present on the person support surface, wherein the computer stores an algorithm for determining a gaze of the subject, determining that a target of the gaze of the subject corresponds to a location of an object, and outputting a notification indicating that the subject is viewing the object.

Clause 42. The vision system of clause 41, wherein the computer is configured to generate the alert upon the subject exiting the person support surface.

Clause 43. The vision system of any one of clauses 41 to 42, wherein the computer is configured to determine how long the subject has been absent from the person support surface and generate the alert upon the determining that the subject has been absent for longer than a predetermined amount of time.

Clause 44. The vision system of any one of clauses 41 to 43, further including at least one sensor positioned on the person support apparatus and communicatively coupled to the computer, wherein the at least one sensor is operable for detecting presence of the subject on the person support apparatus.

Clause 45. A vision system: a computer configured to receive image data and determine a tidal volume of the subject positioned on a person support surface from the image data, wherein the computer is further configured to determine, using the image data, status of health parameters and/or occurrence of a medical event.

Clause 46. The vision system of clause 45, further including at least one camera communicatively coupled to the computer and positioned such that a field of view of the at least one camera captures a health monitor associated with the person support apparatus, and the computer is further configured to determine, using data received from the at least one camera, status of health parameters and/or occurrence of a medical event as indicated by the health monitor.

Clause 47. The vision system of clause 46, wherein the at least one camera is positioned such that the field of view captures a medication associated with the person support apparatus, and the computer is further operable to determine, using data received from the at least one camera, whether the medication needs to be refilled and/or is being administered.

Clause 48. A method of determining tidal volume of a subject on a person support apparatus, the method including: receiving, at a computer, image data indicative the tidal volume of the subject; determining, via the computer, the tidal volume of the subject positioned on the person support surface based on the image data received at the computer; and outputting the tidal volume of the subject.

Clause 49. The method of clause 48, further including monitoring the tidal volume of the subject with a health monitor, wherein the image data is indicative of the tidal volume of the subject displayed on the health monitor.

Clause 50. The method of any one of clauses 48 to 49, further including determining, via the computer, occurrence of a medical event involving the subject based on the image data.

Clause 51. The method of any one of clauses 48 to 50, further including determining, via the computer, whether to refill a medication being administered to the subject supported by the person support surface based on the image data Clause 52. A vision system including: at least one camera positioned such that a field of view of the at least one camera contains a person support apparatus supporting a subject positioned thereon; and a computer communicatively coupled to the at least one camera, the computer configured to receive at least one image from the at least one camera, determine whether the subject is within a predetermined distance from an edge of the person support surface, and generate an alert indicating that the subject is at risk of falling off of the person support surface upon determining that the subject is within the predetermined distance from the edge.

Clause 53. The vision system of clause 52, further comprising at least one sensor positioned on the person support apparatus and communicatively coupled to the computer, wherein the at least one sensor is operable for detecting location of the subject on the person support apparatus relative to the edge Clause 54. The vision system of any one of clauses 52-53, wherein the person support apparatus includes an articulating deck frame and a controller communicatively coupled to the articulating deck frame, the controller being operable to instruct actuation of actuators that articulate the articulating deck frame, wherein the computer is communication with the controller and configured to instruct the controller to articulate the articulating deck frame upon determining that the subject is within the predetermined distance from the edge.

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

What is claimed is:

1. A vision system for a person support apparatus, comprising:

at least one camera positioned such that a field of view of the at least one camera contains both an object and the person support apparatus supporting a subject positioned therein;

a boom coupled to the at least one camera, the boom including a plurality of linkage arms interconnected and coupled to each other via a plurality of motorized rotational joints, and a controller communicatively coupled to an articulating deck frame, the controller being operable to cause actuation of actuators that articulate the articulating deck frame to incline or decline a person support surface of the person support apparatus;

a computer communicatively coupled to the at least one camera, the plurality of motorized rotational joints, and the controller, wherein the computer is configured to:

cause actuation of the one or more of the motorized rotational joints of the boom to adjust the field of view of the at least one camera based on data received from the controller;

cause actuation of the actuators that articulate the articulating deck frame;

receive at least one image from the at least one camera and determine a gaze direction of the subject and a location of the object from the at least one image from the first camera;

determine that the subject is looking at the object based on the gaze direction of the subject and the location of the object; and output a notification when the subject is looking at the object.

2. The vision system of claim 1, further comprising a health monitor associated with the person support apparatus; and wherein the computer is configured to:

determine a tidal volume of the subject positioned on the person support surface from the at least one image; and determine, using data received from the at least one camera, status of health parameters and/or occurrence of a medical event as indicated by the health monitor.

3. The vision system of claim 1, wherein the at least one camera is positioned such that the field of view captures a medication associated with the person support apparatus, and the computer is further operable to determine, using data received from the at least one camera, whether the medication is being administered.

4. The vision system of claim 1, wherein the person support apparatus comprises a plurality of mounting sites for mounting the at least one camera, and the at least one camera is mountable to the person support apparatus at any of the one or more of the mounting sites.

5. The vision system of claim 1, wherein the at least one camera includes a first camera focused on the person support apparatus and a second camera focused on the object, the computer being operatively connected to both the first camera and the second camera, the computer operable to store an algorithm therein for determining the gaze direction of the subject via the first camera, determining that a target of the gaze direction of the subject corresponds with the location of the object monitored by the second camera, and outputting a notification indicating that the subject is viewing the object.

6. The vision system of claim 1, wherein the person support apparatus comprises a head end and a foot end, and the boom comprises a first ends disposed on the head end and a second end coupled to the at least one camera.

7. The vision system of claim 1, wherein the at least one camera is supported on a distal most linkage arm of the plurality of linkage arms.

8. The vision system of claim 1, wherein the computer is integrated within the person support apparatus.

9. The vision system of claim 1, further comprising a mobile cart, and the computer and the at least one camera are disposed on the mobile cart.

10. The vision system of claim 9, wherein the boom couples the at least one camera to the mobile cart.

* * * * *